United States Patent [19]
Shadduck

[11] Patent Number: 6,053,909
[45] Date of Patent: Apr. 25, 2000

[54] IONOTHERMAL DELIVERY SYSTEM AND TECHNIQUE FOR MEDICAL PROCEDURES

[76] Inventor: John H. Shadduck, 1490 Vistazo West St., Tiburon, Calif. 94920

[21] Appl. No.: 09/049,711
[22] Filed: Mar. 27, 1998
[51] Int. Cl.[7] .................................................. A61H 5/06
[52] U.S. Cl. .................................. 606/3; 606/16; 606/48; 606/50; 607/99; 607/101
[58] Field of Search ................................ 606/3, 5, 7, 10, 606/13, 15, 16, 41, 45, 48, 49, 50; 607/89, 93, 98, 99, 101, 117

[56] References Cited

U.S. PATENT DOCUMENTS

| | | | |
|---|---|---|---|
| 4,950,266 | 8/1990 | Sinofsky | 606/7 |
| 5,084,043 | 1/1992 | Hertzmann | 606/3 |
| 5,112,328 | 5/1992 | Taboada | 606/5 |
| 5,263,951 | 11/1993 | Spears | 606/13 |
| 5,334,190 | 8/1994 | Seiler | 606/3 |
| 5,348,551 | 9/1994 | Spears | 606/5 |
| 5,500,012 | 3/1996 | Brucker | 606/15 |
| 5,529,076 | 6/1996 | Schachar | 607/99 |
| 5,591,157 | 1/1997 | Hennings | 606/13 |
| 5,755,753 | 5/1998 | Knowlton | 606/33 |
| 5,827,268 | 12/1998 | Laufer | 606/28 |
| 5,843,073 | 12/1998 | Sinofsky | 606/3 |

Primary Examiner—John P. Leubecker
Assistant Examiner—Ira Hatton

[57] ABSTRACT

An Rf energy applicator with a working end that carries a bi-polar Rf electrode system for creating a Rf-tissue interaction or ionothermal effect in subsurface tissue (a first ionothermal system) which effect is focused by concurrent actuation of a photonic tissue-sensitizing system or photo-conductance system (a second ionothermal system). The photonic energy system is adapted to create a "lens electrode" in subsurface tissue that enhances the targeted tissue's conductance of Rf current which serves as a means of focusing Rf ionothermal effects at a subsurface level. A dosimetry control system is provided that controls the dose and timing of Rf energy delivery as well as the dosimetry of photonic energy delivery. The ionothermal applicator has a handle portion coupled a tubular extending member. The distal termination of the probe has at least one pair of opposing conductive electrodes in a spaced relationship around a perimeter of the distal termination of the extending member. A remote Rf source (or generator) is connected to the device for delivering bi-polar Rf energy to the paired electrodes. An optical fiber (or fiber optic bundle) is provided in a central channel of the extending member which is capable of delivering a photonic (light) beam from a light source, such as a pulsed laser (or continuous wave (CW) diode laser).

9 Claims, 21 Drawing Sheets

IONOTHERMAL DELIVERY SYSTEM AND TECHNIQUE FOR MEDICAL PROCEDURES

BACKGROUND OF THE INVENTION

1. Field of the Invention

This invention relates to medical devices and techniques for low-power Rf (radiofrequency) delivery to develop ionic perturbations in biologic tissue for creating localized thermal effects, such Rf energy being focused in part by simultaneous photonic tissue-stimulation, and more particularly to such a Rf/photonic system for delivering low-power focused thermal effects on subsurface tissue (e.g., on collagenous tissue in a herniated disc to shrink collagen in the annulus fibrosus to reduce the herniation).

2. Description of Related Art

The incidence of disc-related disease is about 1.7 percent of the general population, affecting an estimated 85 million people worldwide. Up to 80% of those of suffering can be treated with conservative measures such as anti-inflammatory drugs, muscle relaxing drugs, acupuncture or bed rest. The remaining 20% of the patient population may be candidates for a more aggressive therapies, which include surgeries. The primary surgical approach for a prolapsed or herniated disc has been to remove the offending disc (diskectomy). In this procedure, most or all of the prolapsed disc is resected, at times with a portion of the overlying bone. Such open surgeries have a success rate of 50%–60% or more in reducing lumbar pain. Long-term outcomes, however, are called into question because there are often degenerative changes in both the disc and surrounding bones following such a disk surgery.

The structural elements of the spinal column include the vertebrae interleaved with cartilagenous disc. The discs consist of a substantially hard outer ring of tissue called the annulus fibrosus, made of concentric layers of the crisscrossed fibrous cartilage which is predominantly collagen. Contained within the annulus fibrosus is a gelatinous highly elastic core, called the nucleus propulsus that has a high water content. The nucleus propulsus serves as the shock absorber of the spine to cushion compression loads on the vertebrae. The nucleus propulsus, together with the annulus fibrosus, also form a "ball bearing" within the spine to allow rotation and flexion. In the aging process, the water content in the nucleus propulsus typically decreases which makes the surrounding cartilage more deformable. Flexion of the spine causes uneven compression of the discs and can cause the nucleus propulsus to rupture or herniate the annulus propulsus. When a protrusion or herniation of the annulus propulsus impinges on a nerve root or the spinal cord, the patient may experience extreme pain in the back or legs. Such pain is often the first is sign of a disc disorder.

It is known in the art that mono-polar high-energy radiofrequency (Rf) energy probes can be used to shrink collagen in cartilagenous tissues (e.g., in joint capsule shrinkage procedures) where Rf is delivered to tissue between the mono-polar electrode at the end of a Rf probe and a groundplate. The prior art techniques involve "instantaneous" collagen shrinkage with a high energy Rf delivery (estimated 40 to 60 watts). It is unlikely that such a mono-polar Rf probe could be safe and effective for treating disc tissue, because thermal energy must be very precisely delivered. Such high energy mono-polar Rf probes suffer from several significant drawbacks.

A first disadvantage relates to the electrode dimension which is limited by the size (diameter) of the probe. When using a small diameter probe (e.g., 1.5 mm. to 3.0 mm. for percutaneous disc treatments) the electrode would have little surface area which means that Rf current intensity necessarily would be high (est. 40 to 60 watts) in order to emit Rf waves sufficient to perturb ions (to increase temperature) within a subsurface collagenous layer. Such high Rf energy levels would easily be capable of ablating or perforating surface of the tissue, which would be highly undesirable.

A second disadvantage of a high-energy mono-polar probe relates to the technique of its use which typically includes "painting" the hot probe tip across an overlying tissue layer or surface (e.g., a cartilage) in an effort to delivery thermal energy to a underlying collagenous layer. Again, typical Rf energy levels would necessarily be high (est. 40 to 60 watts) for the Rf to elevate the temperature of subsurface tissue layers since the probe is moving. It must be recalled that Rf energy causes thermal effects in biologic tissue by perturbation of ions as alternating Rf energy courses through the tissue in paths of least resistance between an active mono-polar Rf electrode and the groundplate. "Painting" the hot probe tip across a tissue surface causes the Rf paths through tissue to change constantly thus preventing the perturbation of ions in any particular path or location—thus preventing effective energy densities (temperature elevation) in any particular location to affect collagenous tissue. As can be seen in FIG. 1A, the Rf current paths are localized only momentarily and are not focused on the collagenous layer targeted for ionic perturbation. FIG. 1B shows the typical thermal gradient in tissue which is created by a high-energy mono-polar probe at a moment in time where higher temperatures are closer to the electrode. Thus, the prior art devices and methods must use a very high current intensity (to create high enough energy densities) to achieve "instantaneous" collagen shrinkage consistent with the painting technique.

What is needed is a technique and instrument for elevating the temperature of subsurface collagenous tissue (e.g., in a disc) that preferably (i) utilizes relatively low Rf power levels to prevent surface tissue ablation, (ii) utilizes bi-polar Rf flow (rather than mono-polar flow) to maintain the energy density in localized tissue (rather that between a mono-polar electrode and a remote groudplate); (iii) includes means to focus the paths of bi-polar Rf current flow within particular subsurface collagenous layers; (iv) includes means to create a more even thermal gradient between the tissue surface and the deeper collagenous tissue, and; (v) allows for observation of the shrinkage of collagenous tissue at a controlled rate that is slower than the prior art "instantaneous" rate of collagen shrinkage.

SUMMARY OF THE INVENTION

The present invention involves a system for delivering bi-polar Rf current to subsurface biologic tissues from a small cross-section probe for tissue temperature-elevation purposes, and is disclosed in an exemplary procedure for shrinking collagenous tissue (e.g., in a disc between vertebrae to reduce a disc herniation). The system additionally utilizes a photonic energy means to create a "lens electrode" within a subsurface layer to focus a "low-power" Rf current on targeted tissue, for example to attain a collagen shrinkage temperature range.

As background, it should be understood that "bi-polar" Rf electrode arrangements have been developed for many uses, such as for coagulating tissue engaged by the working end of a scissors or graspers. However, the use of bi-polar Rf energy delivery has not been adapted for small diameter probes designed for "topical" Rf delivery applications. In the use of a "small" probe tip (e.g., 1 mm. to 5 mm.) that carries paired electrodes for bi-polar flow in a topical application, the Rf current probably would flow from electrode-to-electrode along a conductive path in the tissue surface immediately upon tissue contact (see FIG. 2A). In other words, the thermal effects would not extend below the surface issue layer (i.e., the bi-polar probe would cause any significant ionic perturbation at any significant tissue depth unless current intensity were very high as shown in thermal gradients of FIG. 2B).

There may be few medical treatments requiring topical access to a underlying collagenous layer through an overlying surface tissue layer, wherein a small diameter topical Rf applicator system is desirable or required. Thus, the present invention may be adapted only for a specialized purposes, one of which is access to a herniated site of an intervertebral disc through the nucleus propulsus (see FIGS. 9 & 10A). Such a disc treatment involves reducing the disc herniation by shrinking portions of the collagen matrix layer within the annulus fibrosus. The shrinking effect is caused by raising the temperature of collagen in a subsurface disc portion to the range of 55° C. to 70° C.

A disc contains a substantial amount of collagen which is one of the most abundant proteins in the human body. It is well-known in the art that collagen fibrils will shrink longitudinally when subjected to temperatures ranging above about 60° C. Interstitial collagen consists of a continuous helical molecule made up of three polypeptide coil chains. Each of the three chains is approximately equal in longitudinal dimension with the molecule being about 1.4 nanometers in diameter and 300 nm. in length along its longitudinal axis in the helical domain portion. Collagen molecules polymerize into chains in a head-to-tail arrangement generally with each adjacent chain overlapping another by about one-forth the length of the helical domain. The spatial arrangement of the three peptide chains is unique to collagen with each chain existing as a right-handed helical coil. The superstructure of the molecule is represented by the three chains being twisted into a left-handed superhelix. The helical structure of each collagen molecule is bonded together by heat labile cross-links between the three peptide chains providing the molecule with unique physical properties, including high tensile strength and limited longitudinal elasticity. The heat labile cross-links may be broken by thermal effects thus causing the helical structure of the molecule to be destroyed (or denatured) with the peptide chains separating into individually randomly coiled structures of significantly lesser length. The thermal cleaving of such cross-links may result in contraction or shrinkage of the collagen molecule along its longitudinal axis by as much as one-third of its original dimension. In the exemplary disc procedure disclosed herein, it is such thermal shrinkage of the collagenous cartilage tissue that can reduce the herniation of the disc.

Collagen fibrils will shrink within a specific temperature range, (e.g., 55° C. to 70° C.) depending on the type of collagen. The shrinkage temperature of collagen has been variously defined, such as: the particular temperature at which the helical structure of the collagen molecule is denatured; a particular temperature at which ½ of the helical superstructure is lost; or, the temperature at which collagen shrinkage is greatest. In fact, the concept of a particular collagen shrinkage temperature is less than meaningful. Such thermally-induced shrinkage of collagen can depend not only on an actual "peak" temperature, but it is believed can be based on a time/temperature increase profile (increase in temperature at a particular rate; maintenance at a particular temperature over a period of time, etc.). In other words, it is known that collagen shrinkage can be attained through high-energy exposure (energy density) for a very short period of time to attain "instantaneous" collagen shrinkage as in the prior art (prior art treatments all have been adapted to shrink collagenous tissue instantly, or in a matter of seconds, at most). Alternatively, it is believed that another manner of collagen shrinkage exists and is disclosed herein. It is believed that a lower rate of collagen shrinkage can be attained at a lower particular temperature (all other tissue characteristics remaining equal) than required for "instantaneous" shrinkage, provided that for such "low-rate" collagen shrinkage the targeted tissue is maintained at the particular lower temperature for a longer period of time, as will be described below in a method of the invention.

The Rf probe or applicator of the invention has a working end that carries a bi-polar Rf electrode system for creating a Rf-tissue interaction which is herein more precisely described as an ionothermal effect (a first ionothermal system). The applicator's working end also carries a photonic tissue-sensitizing system (or photoconductance system) for creating a "lens electrode" in the tissue that enhances the targeted tissue's conductance of Rf current as a means of focusing the ionothermal effects of the Rf-tissue interaction at a subsurface level (a second ionothermal system). A dosimetry control system is provided that controls the "dose" of Rf current and the timing of Rf delivery and photonic energy delivery (and photonic energy dose).

The ionothermal Rf probe has a handle portion coupled a tubular extending member. The distal termination of the probe has paired opposing conductive electrodes in a spaced relationship around a perimeter of the distal termination of the extending member. A remote Rf source (or generator) is connected to the device for delivering bi-polar Rf energy to the electrode pair. An optical fiber (or fiber optic bundle) is provided in a central channel of the extending member which is capable of delivering a photonic (light) beam from a light source, such as a pulsed laser (or continuous wave (CW) diode laser). An important element of a method of the invention is to deliver a photonic (light) beam that is adapted to penetrate to a particular desired depth in tissue before being absorbed to create the "lens" electrode effect, together with a power level adapted to develop the optimal range of energy density in the targeted tissue.

As background relating to Rf-tissue interaction, the bi-polar Rf system disclosed herein utilizes a high frequency alternating Rf current (e.g., from 25,000 Hz to 600,000 Hz) that is adapted to flow between the paired bi-polar electrodes at the device's distal end. The alternating current causes ionic perturbation along current paths within tissue which elevates the tissue temperature as ions follow the changing directions of the alternating current. Such ionic perturbation causes thermal effects (ionothermal effects) in manner different from tissue contact with a resistive electrode. In the delivery of such Rf energy to a soft tissue mass, I=E/R where I is the intensity of the current in amperes, E is the energy potential measured in volts and R is the tissue resistance measured in ohms. In a targeted soft tissue, current density (or energy density) is an important gauge of energy delivery which further relates to the impedance of the target tissue mass. The level of ionothermal effects within the target tissue volume thus is influenced by several factors, such as (i) RF current intensity, (ii) RF current frequency, (iii) impedance levels of tissue between paired electrodes, (v) heat dissipation from the target tissue volume; (vi) duration of Rf delivery, and (vii) distance through the targeted tissue volume between the paired bi-polar electrodes.

As background related to the photonic-tissue interaction for creating the "lens electrode" effect in tissue, it should be appreciated that prior art medical uses of photonic (light) energy cause photonic-tissue interactions that fall into two basic modalities: photodisruption and photocoagulation. (The invention herein discloses a third novel modality: photoconductance). In the prior art photodisruption category, a high energy photon (light) device, such as a laser, delivers an intense light pulse into a biologic tissue that generates a plasma by ionization of the atoms in the targeted tissue. The creation of such a plasma set off shock waves and other effects that destroy cells in the targeted tissue. Such photodisruption procedures cause high energy densities in tissue, which are thus unrelated to the wavelength absorption spectrum of the targeted tissue. In the prior art photocoagulation category, a photonic (light) energy source, such as a laser, is used to heat tissue to the point of ablation, welding or melting. For example, laser energy is produced at a particular level that elevates tissue temperature to a point below that required to create a true plasma (as in photodisruption). The effects of such thermal photocoagulation relate to the wavelength-dependent absorption of photonic energy in the targeted tissue.

In the modality of photonic-tissue interaction disclosed herein (photoconductance or photosensitization), a very low energy density is developed in tissue by directing a low level of photonic (light) energy into the targeted tissue. A particular objective of such photonic-tissue interaction is to prevent the high "peak" temperature in tissue created by pulsed lasers, and to control the related rate of increase in temperature (time/temperature profile). Such localized tissue sensitization enhances the conductance (decreases impedance R (resistance in ohms)) of the irradiated target tissue to the fluence of Rf current (current density). Hence the term "lens electrode" is defined herein as a tissue portion that has an enhanced conductivity to electromagnetic energy flow for any reason. Such localized or focused photosensitization, it is believed, alters the impedance of the localized tissue to thus "induce" localized bi-polar Rf current flow through the affected or sensitized tissue. In other words, the photoconductance effect creates a region of lesser resistance (R) between the bi-polar electrodes. This proposed modality of photo-sensitization of tissue is timed to occur simultaneous to the initiation of Rf current flow, or preferably slightly prior to the initiation of Rf current flow.

The depth of penetration of photonic energy to create the lens electrode effect is wavelength-dependent, which has been developed in the prior art of the photocoagulation modality. Laser applications have been developed at particular wavelengths since there is a region of the light spectrum, in the red and near infrared ranges, where biological tissue is mostly transparent to light. This transparent region lies between the visible (where chromophores in tissue such as hemoglobin are strongly absorbing) and the infrared (where water within tissue is absorbing) and is sometimes referred to as a tissue-wavelength window.

Biologic tissue (e.g., annulus fibrosus) typically has a high percentage water content. In the absence of pigmentation within such biologic tissue, the tissue's water content largely determines its absorption of light. The absorption coefficient of water at its peak is around 3 microns ($\alpha$=1.3 cm.$^{-1}$). To photosensitize the subsurface tissue of an annulus fibrosus to create the lens electrode effect, it is important to select a light wavelength that penetrates through the surface layer interface between the fluid of the nucleus propulsus and the annulus fibrosus to a particular depth in the annulus before absorption. The preferred light beam (coherent or non-coherent) operates in the infrared portion of the spectrum, preferably radiating at a wavelength of from about 1.30 to 3.00 microns. For example, a laser having a wavelength of 1.44 microns coincides with a strong water absorption band, and light at 1.44 microns wavelength is extinguished by water after passing about 0.3 mm. into the water. This range is preferable for the technique of disc treatment but other wavelengths may be suitable for other tissues. Thus, different light wavelengths (whether coherent or non-coherent) may be suitable for sensitizing tissue for enhancing the effects of bi-polar Rf delivery, such as the annulus fibrosus discussed in the method of the invention herein, depending on the depth desired for the photoconductance effect. The beam widths may be from about 0.01 mm. to 3.0 mm. or more. (There are smaller peaks of the absorption coefficient that may be suitable for achieving a useful depth of penetration: e.g., a Holmium:YAG laser emission (at 2.1 microns; $\alpha$=50 cm.$^{-1}$) or the Neodinium:YAG laser's emission (at 1.06 microns; $\alpha$=about 1.0 cm.$^{-1}$) respectively where absorption depth=1/$\alpha$.).

The technique of creating a "lens" electrode in tissue to focus the path Rf current flow thus prevents stray Rf flows and allows lower power levels to achieve significant temperature elevation. The Rf current flow also provides for a much more even thermal gradient in tissue (depthwise) thus heating collagenous tissue to a greater depth than the prior art mono-polar devices.

In general, the novel systems and techniques of the present invention allow bi-polar Rf energy delivery for elevating temperatures in subsurface tissue layers in a manner that not over-elevate temperatures in overlying tissue layers.

The systems and techniques of the present invention allow bi-polar Rf energy delivery to be focused in subsurface tissue layers in a manner that would not be possible without a hybrid system that induces ionothermal effects in such subsurface tissues.

Other objects and advantages of the invention will be apparent from the following description, the accompanying drawings and the appended claims.

BRIEF DESCRIPTION OF THE DRAWINGS

FIG. 1B being a view similar to FIG. 1A illustrating the thermal gradient in the tissue mass attained by the mono-polar Rf current delivery of FIG. 1A.

FIG. 2B being a view similar to FIG. 2A illustrating a typical thermal gradient created by the bi-polar current delivery of FIG. 2A.

FIGS. 8A–8E are schematic sectional views of the sequential manner in which Rf energy is delivered to biologic tissue with photoconductive enhancement; FIG. 8A showing a biologic tissue mass in its native state with a targeted subsurface collagenous tissue layer; FIG. 8B depicting the tissue mass irradiated with a photonic beam in a photoconductance step of the invention; FIG. 8C depicting the tissue mass irradiated with photonic energy with a simultaneous fluence of Rf energy through the photosensitized tissue; FIG. 8D depicting the tissue mass after termination of both photonic energy delivery and the Rf current delivery showing the resulting confluence or energy density in the targeted tissue.

FIG. 10A showing a pathology indicative of single-location disc herniation; FIG. 10B depicting the distal end of the probe inserted through the annulus propulsus to the site of the herniation; FIG. 10C showing the herniation reduced by thermally assisted shrinkage of the collagenous annulus fibrosus.

DETAILED DESCRIPTION OF THE INVENTION

1. Type "A" Embodiment of Ionothermal System

Figure 1A:
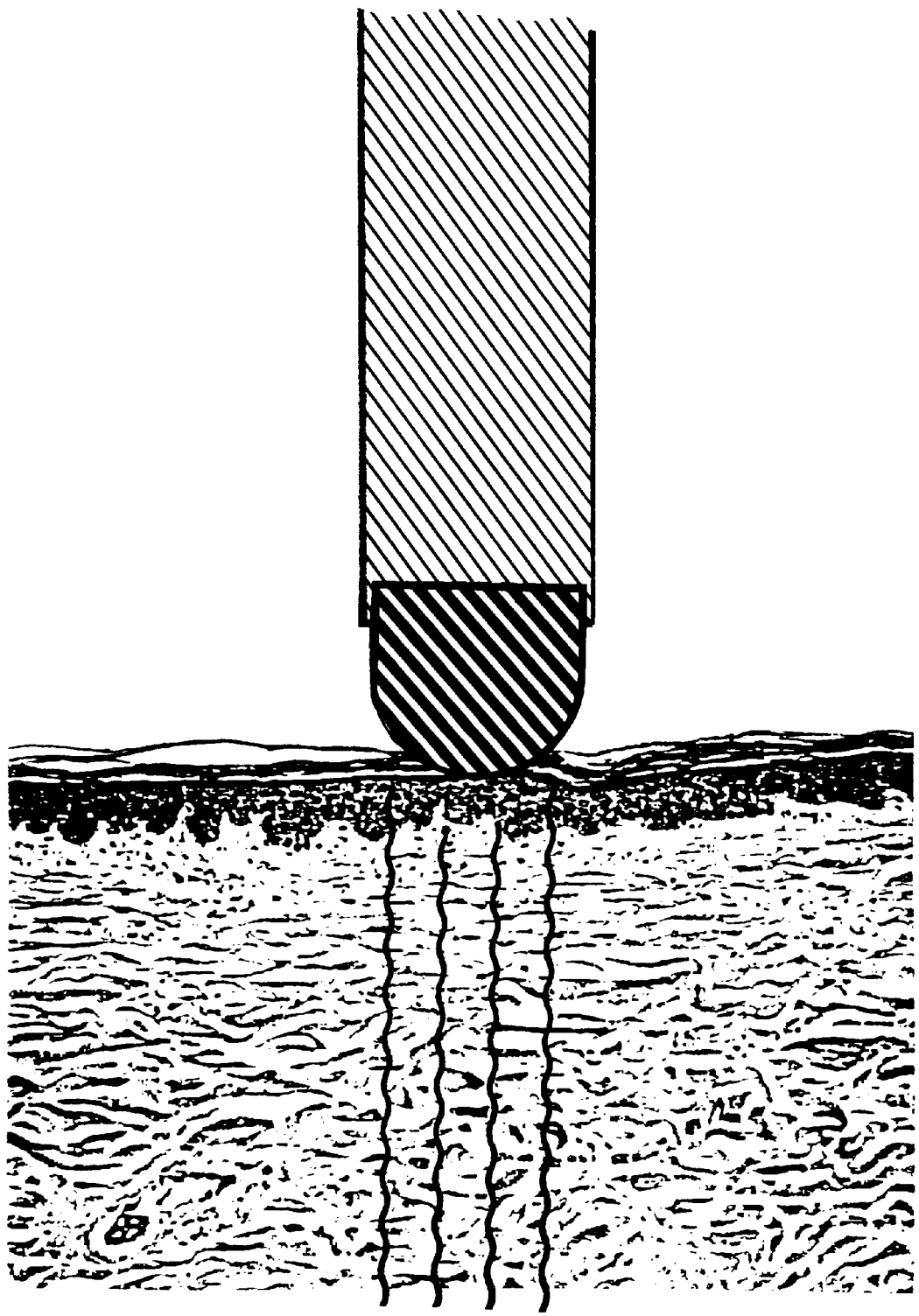
FIGS. 1A–1B are schematic views of a prior art method of high-energy mono-polar Rf energy delivery to a tissue mass, FIG. 1A being a view of an overlying tissue surface and underlying tissue layer indicating directions of mono-polar Rf current flow to a ground.
Figure 1B:
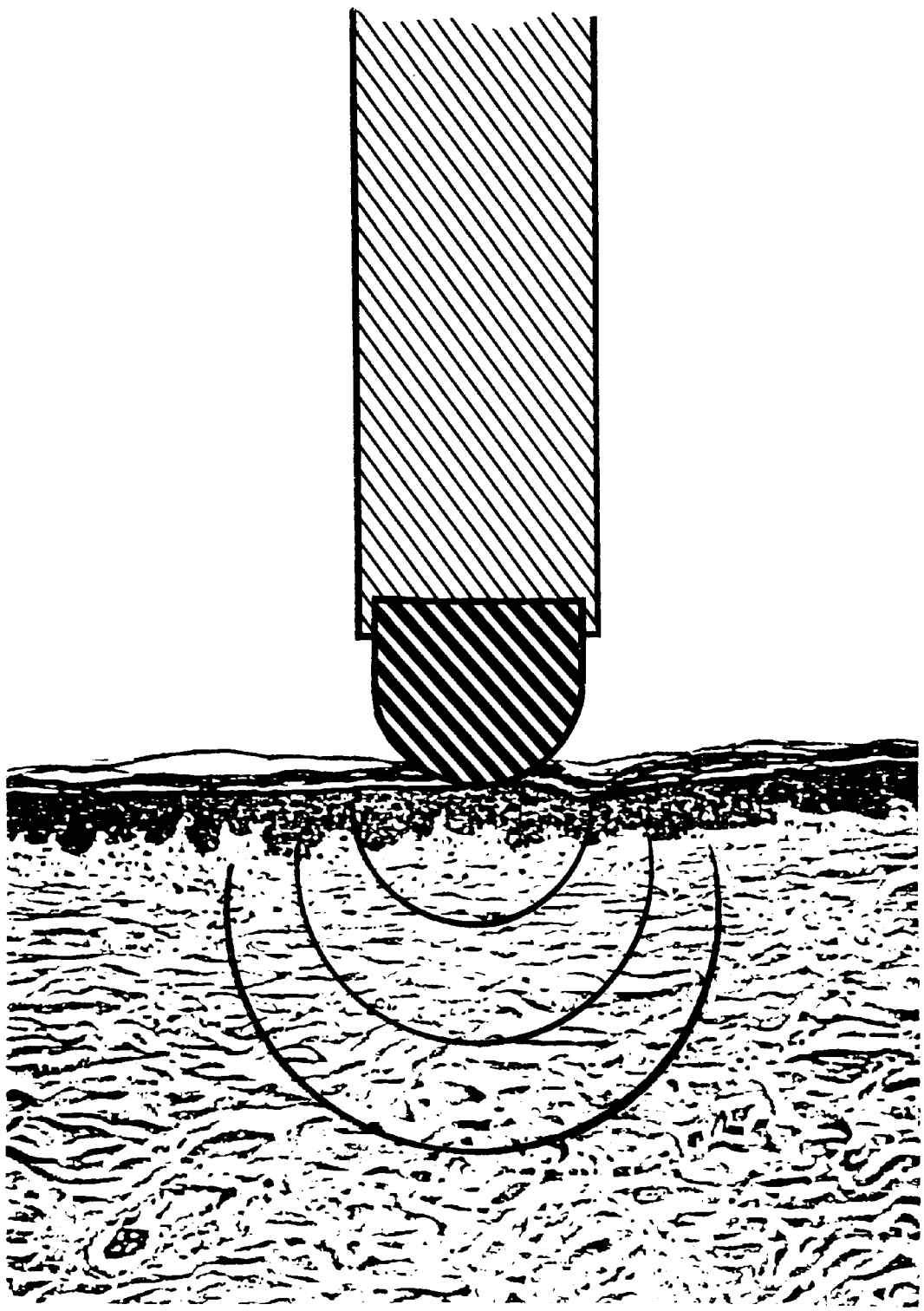
Figure 2A:
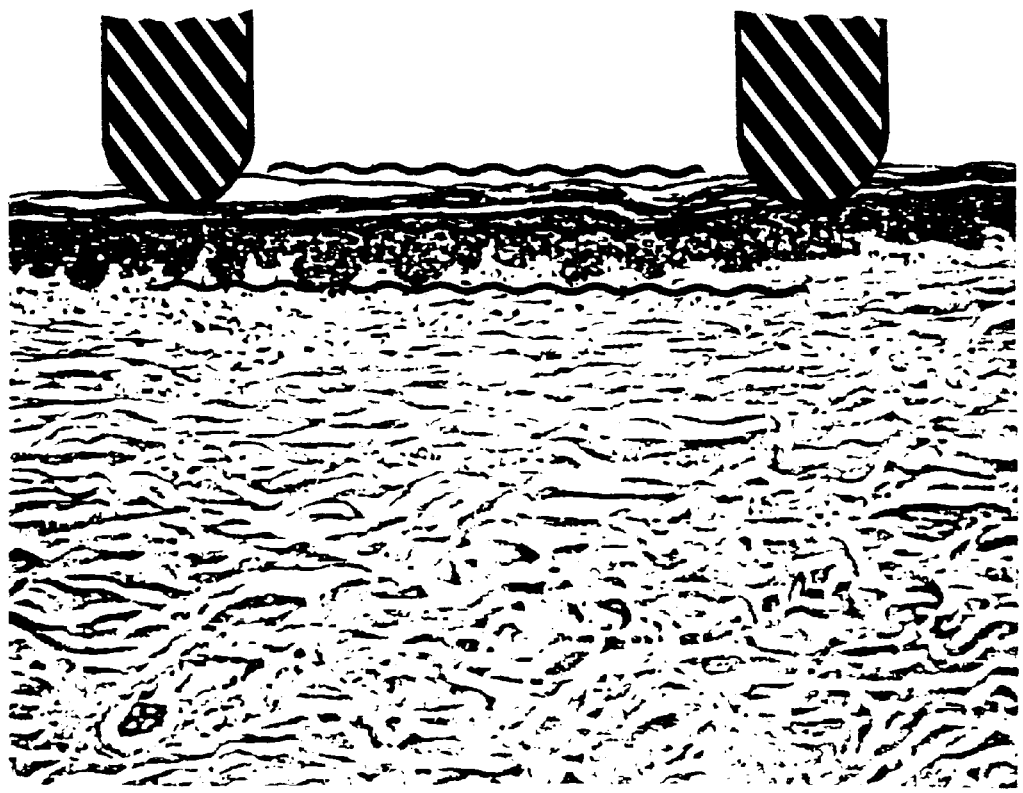
FIGS. 2A–2B are schematic views of a method of high-energy bi-polar Rf energy delivery to a tissue mass, FIG. 2A being a view of the tissue surface and underlying tissue indicating directions of bi-polar Rf current flow.
Figure 2B:
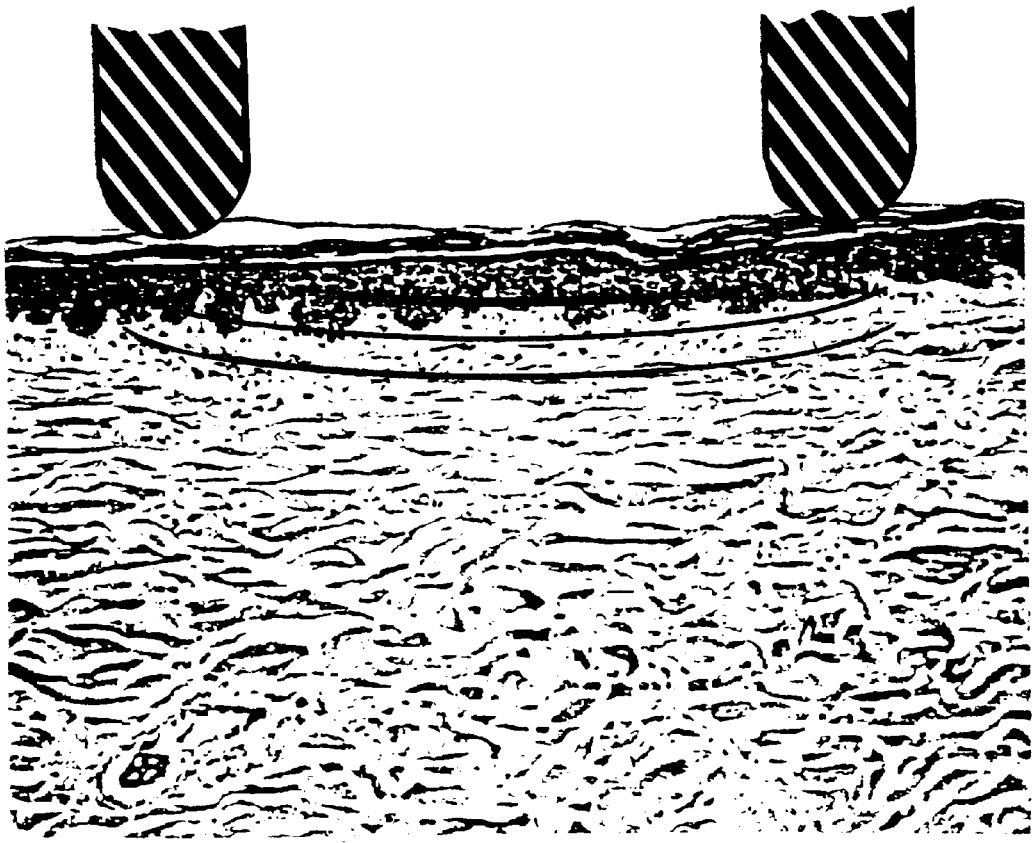
Figure 3:
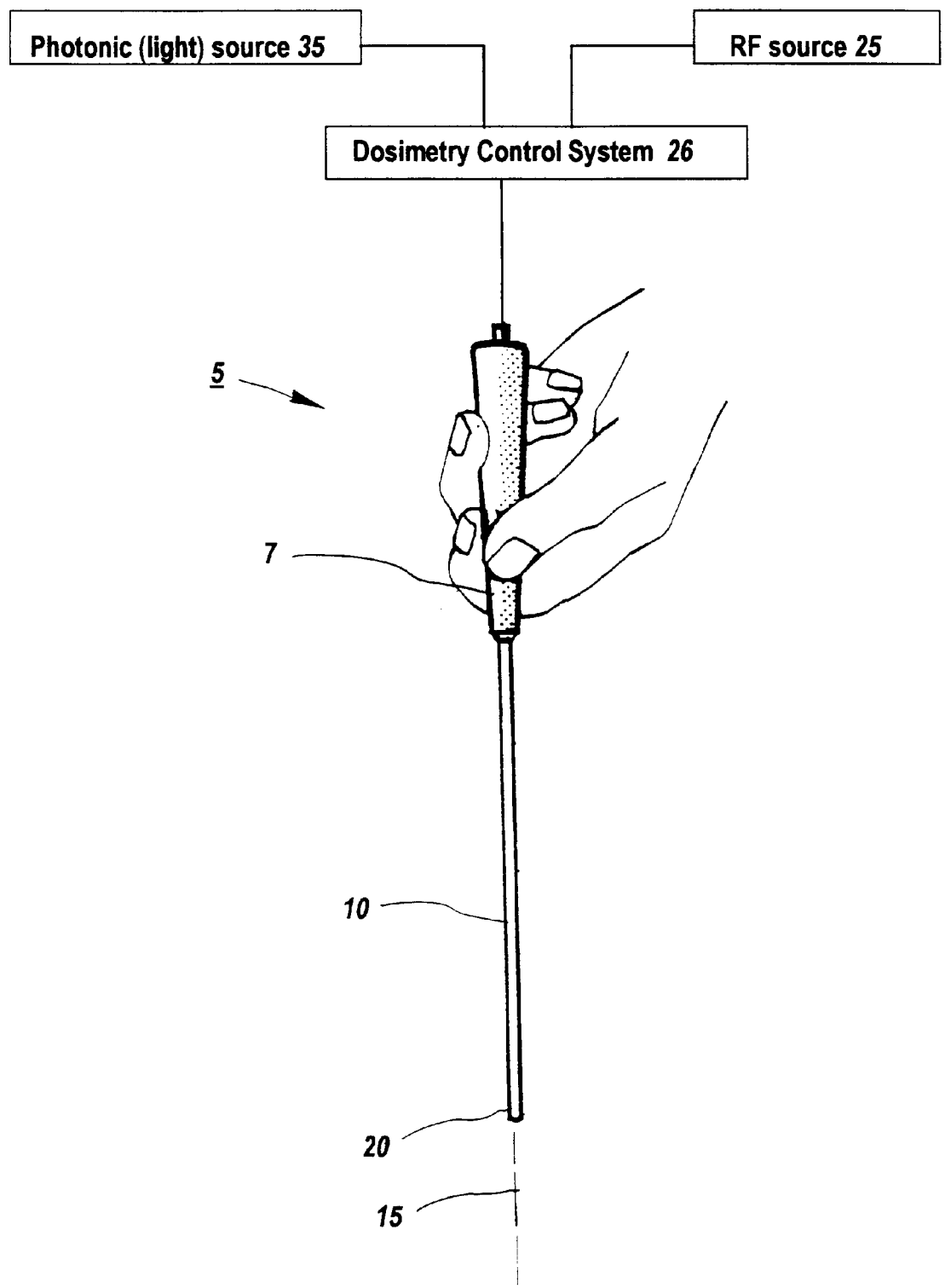
FIG. 3 is a perspective view of the probe of the present invention.
Figure 4:
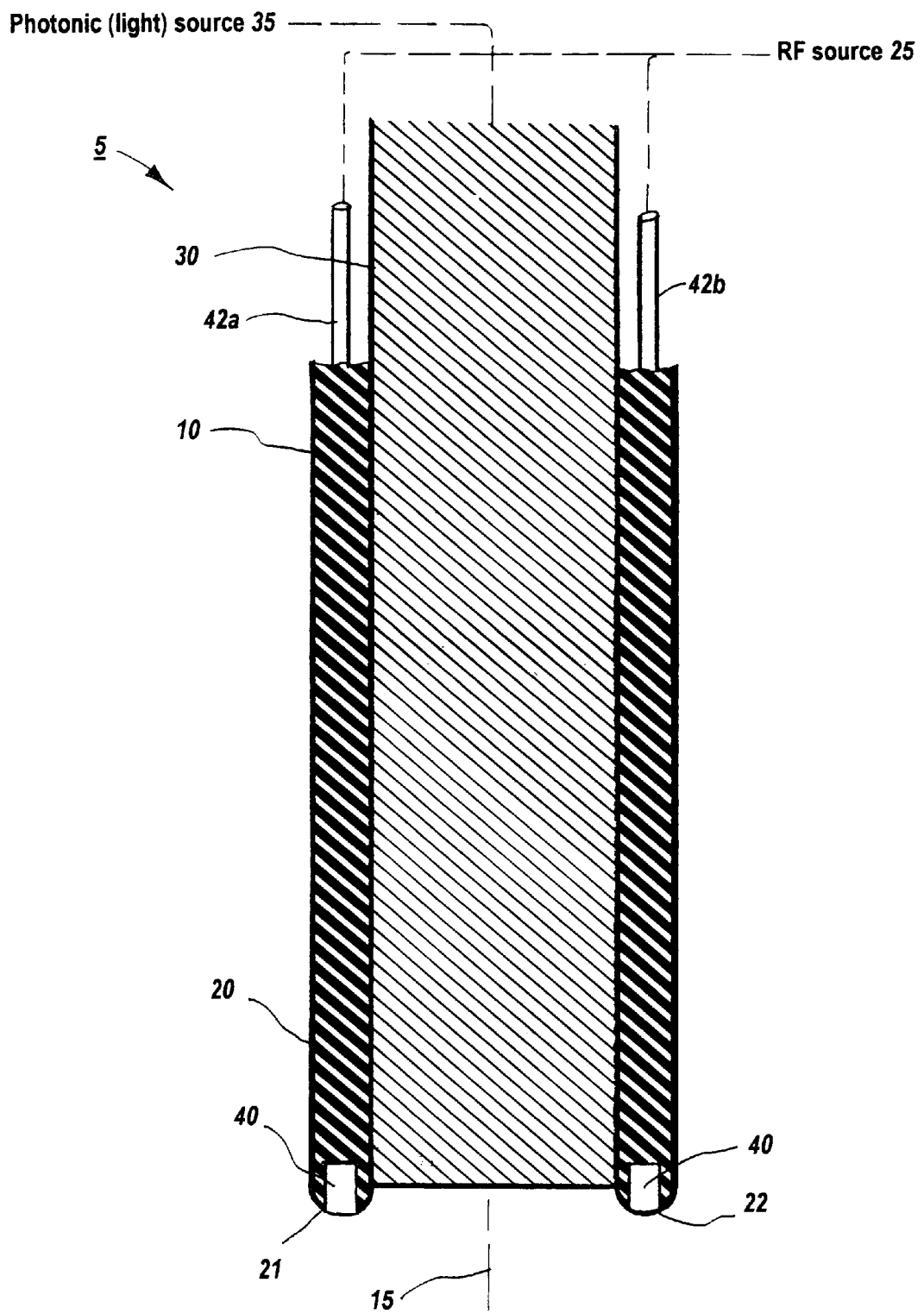
FIG. 4 is an enlarged perspective view of the distal end of the probe of FIG. 3 showing the electrode-carrying member in another position.
Figure 5:
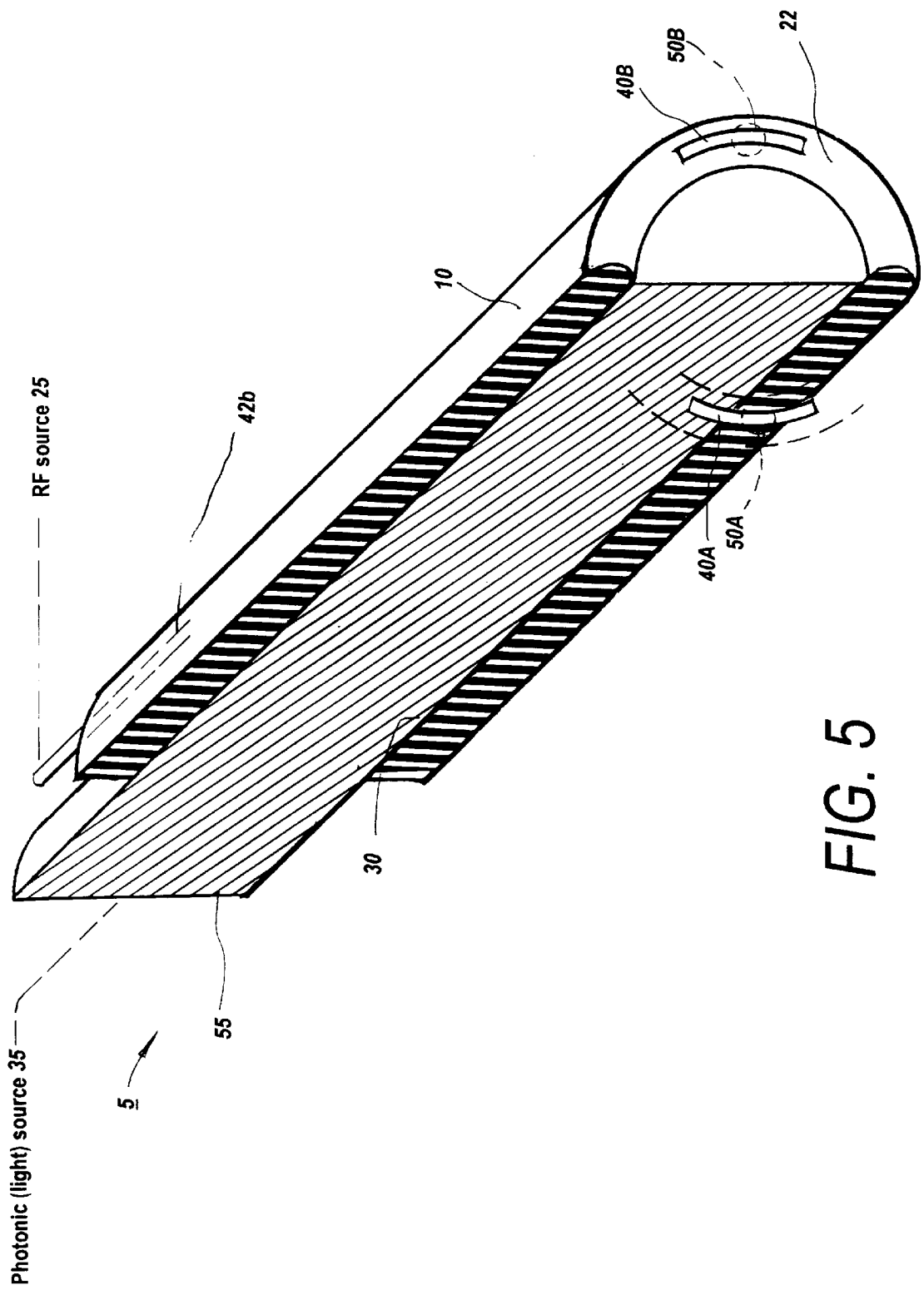
FIG. 5 is an axionometric view of the distal end of the probe of FIG. 4 showing bi-polar electrodes.

Referring to FIGS. 3–5, a handpiece of a Type "A" embodiment of the system of the present invention is shown that is adapted for ionothermal treatment of a patient's herniated disc, although it could be adapted for similar treatment of other tissues. As can be seen in FIG. 3, the ionothermal treatment system includes applicator 5 with handle portion 7 coupled to extension member 10 that extends along central axis 15 to distal working end 20. The working end 20 of applicator 5 carries Rf energy delivery means that are coupled by Rf power transmission cable 24 to remote Rf source (generator) 25 and dosimetry control system 26 (which includes hardware and software described further below). FIG. 3 shows that extension member 10 is tubular and straight but it should be appreciated that extension member 10 may be curved member or even articulatable member with any suitable cross-section to reach any particular tissue and fall within the scope of the present invention. The working end 20 also may have a non-round plan form, such as a simple oval or very elongate oval. The extension member 10 may be any suitable diameter, for example 1 mm. to 5 mm. or more, and is shown in approximately 2 mm. diameter with a length sufficient to reach the targeted disc tissue. Extension member 10 can may be of any suitable non-conductive material such as a medical grade plastic.

Now referring to FIGS. 4 & 5, the greatly enlarged views of working end 20 of applicator or probe 5 show distalmost termination 21 of extension member 10 having radiused perimeter surface portion 22. FIG. 5 shows perimeter surface 22 circumscribing axial channel 30 that carries photonic (light beam) energy from a light source 35 as will be described below. It should appreciated that the plane of perimeter surface 22 may be angled or perpendicular relative to axis 15 of extension member 10 and is shown in this embodiment at a 90° angle to axis 15.

Referring still to FIGS. 4 & 5, applicator 5, and more particularly working end 20, carries two cooperating (first and second) working systems for creating an energy density in targeted tissue: The first or primary system includes bi-polar Rf electrode array 40 that is carried within perimeter surface 22 for delivering Rf current to a targeted tissue to develop a Rf-tissue interaction resulting in an ionothermal treatment aspect of the invention. The second system comprises a photonic tissue-sensitizing system (or photoconductance system) emitting radiation at working end 20 which relates to a pre-treatment aspect of the present invention, by which is meant that certain bio-electrical characteristics of the targeted tissue volume are altered before (or simultaneous to) Rf current delivery to optimize the effects the Rf-tissue interaction. The dosimetry control system 26 also is provided that controls the "dose" of Rf energy delivered to the targeted (photoconductance-enhanced) tissue in different manners or sequences. The systems are described in order below.

(a). Bi-polar Rf Electrode Array of Applicator

The Rf energy delivery system carried in working end 20 comprises an electrode array 40 of paired opposing conductive electrodes 40A–40B in a spaced circular relationship around perimeter surface 22 of the working end 20 (see FIG. 5) The exemplary embodiment of applicator 5 is shown with two conductive electrodes, but it should be appreciated that the electrodes may number from 2 to 4 (or more) and are operated in a bi-polar manner as described below. Each electrode 40A–40B is individually connected by current-carrying wires 42a–42b to Rf source 25. Wires 42a and 42b extend through extension member 10 to handle 7 (see FIG. 3). Electrode material may include gold, nickel titanium, platinum, stainless steel, aluminum and copper. Referring to FIG. 3, power transmission cable 24 is connected via detachable coupling 46 in handle 7 and to the Rf source. The electrode array 40 is energized by any suitable means such as a foot pedal trigger 47 (FIG. 3).

The dosimetry control system will be described in detail below in Section 1 (c). Some aspects of the dosimetry control system are fed by signals from sensors in working end 20. Therefore, referring to FIG. 5, it can be seen that a temperature sensor array of individual thermal sensors 50A–50B is provided with each sensor carried in contact with each electrode 40A–40B. (It should be appreciated that these sensors may be carried in any spaced relationship around perimeter 22 for tissue contact but shown being adapted for measuring the actual temperature of each electrode). Each sensor typically is a thermocouple or thermisters (temperature sensor that has resistances that vary with the temperature level). Thermocouples typically would consist of paired dissimilar metals such as copper and constantan which form a T-type thermocouple.

(b). Photoconductance System of Applicator

Figure 6:
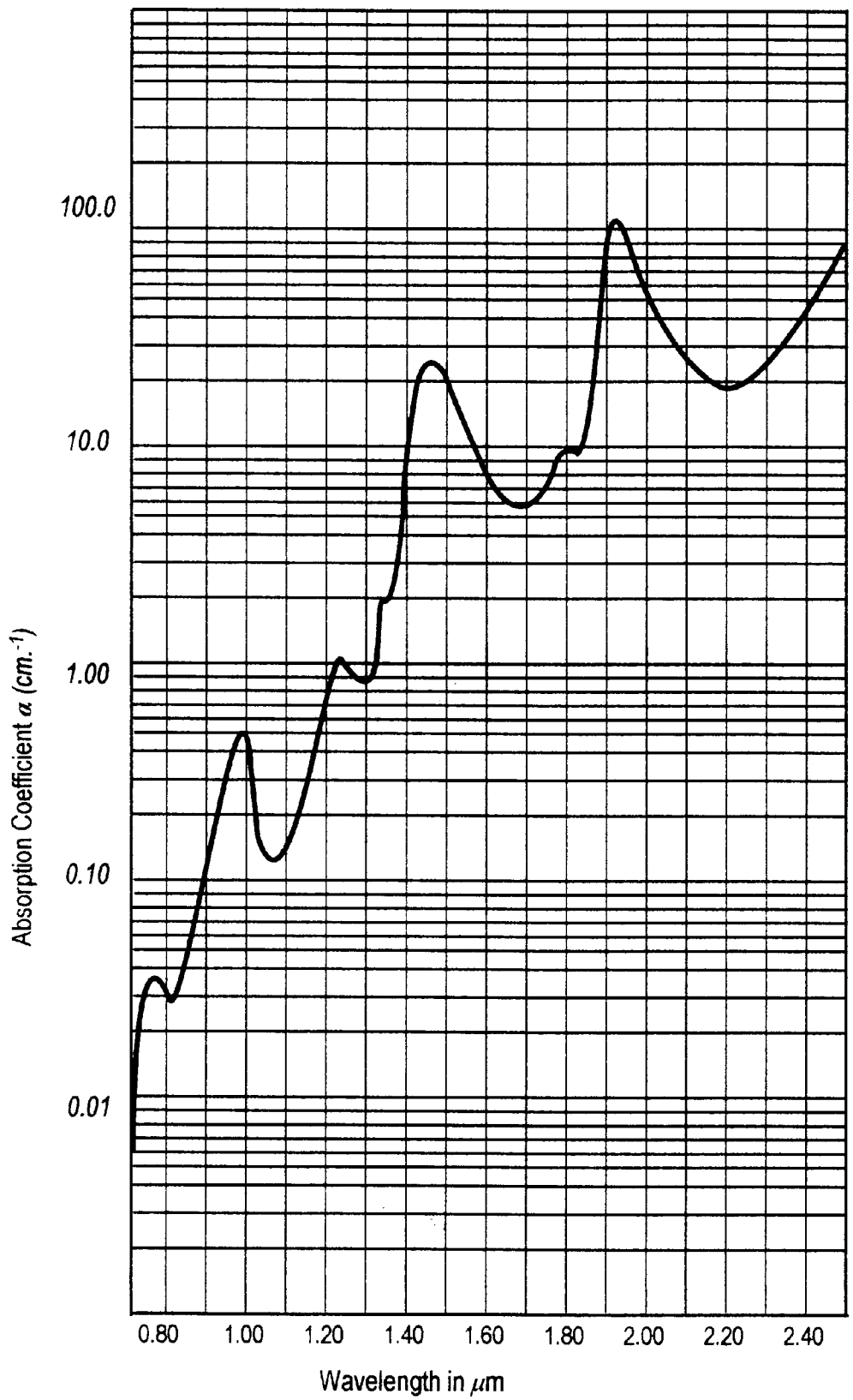
FIG. 6 is graph depicting the absorption coefficient of water in cm-1 vs. wavelength of photonic emissions from a light source of the invention.

The probe 5 carries an optical fiber 55 (or fiber optic bundle or other light-channeling means) in central channel 30 of extension member 10 which is adapted to direct a photonic (light) beam from light source 35. It should be appreciated that any photonic energy (light) source 35 may be suitable for projecting a light beam distally from working end 20, provided the wavelength is suitable for sensitizing tissue in a method of the invention described below. The photonic (light) beam radiated from source 35 may be coherent or non-coherent operating in the infrared portion of the spectrum, preferably radiating at a wavelength of from about 1.3 to 3.0 microns. FIG. 6 is a graph of the absorption coefficient vs. wavelength for water, which is a suitable absorption model for collagenous matrix layer, for example, in the annulus propulsus which is comprised mostly of water. The emission may be pulsed or continuous wave (CW). (Pulsed laser radiation sources include Holmium:YAG; Neodinium:YAG and Erbium:YAG types of lasers). In the preferred embodiment of extension member 10, the beam spot widths may be delivered through channel 30 and optical fiber 55 to provide a beam (spot) width from about 1.0 mm. to 2.0 mm., but spot widths as small as 0.05 mm. may be suitable to accomplish a method of the invention. Preferably, the photonic source 35 will delivery energies of about 0.01 mJ. to 10.0 mJ. per pulse. In a coherent source 35, pulse trains of 0.01 nanosecond to several hundred microseconds with a repetition rate of 0.1 to 20 Hz can be used.

The photonic (light) source 35 is adapted to operate at a low energy level that, if operating alone, would produce energy densities in an underlying tissue layer well below the level that would result in tissue coagulation, ablation or photodisruption. It is necessary that the light energy be absorbed by the tissue layer containing collagen to sensitize the layer to Rf current flow therethrough, but not to so strongly as to photonically injure the tissue, for example to the extent that would induce an inflammatory response. Such a wound-healing response could cause undesirable effects, for example causing the synthesis of new scar (collagen matrices) in the injured tissue.

Another embodiment of the photonic (light) sources can use a continuous wave (CW) diode laser. In using a such diode that emits continuous radiation, it is possible to select a frequency in the desired range as described above along with the desired output. The diode laser can operate continuously (or intermittently) for times desired thus eliminating possible undesirable effects of short pulses, for example, one such characteristic is that a pulsed laser may cause shock waves. Such shock waves generally are to be avoided since they possibly could disrupt tissue or collagen fibers to a significant extent at the exposure site. A diode laser is compact and can be easily operated by an electronic control system and the mid-infrared radiation can be introduced into an optical fiber easily with a loss. Hence, the diode laser can be substituted for the pulsed laser in the embodiment discussed above. A diode laser having a continuous wave (CW) may be turned off intermittently to provide a pulsed delivery, for various reasons such as adapting to the thermal relaxation time of tissue. Further, it should be appreciated that any form of non-coherent light source may be used when filtered to the appropriate wavelengths to develop the photoconductance effect of the method of the invention.

(c). Rf Dosimetry Control System

The dosimetry control system 26 (see FIG. 7) is adapted to time Rf power delivery to electrode array 40 in various sequential operational modes. A preferred operational mode relates to an intermittent Rf delivery aspect of the invention's method. Another optional operational mode relates to feedback signals from sensor array 50 and electrode array 40. The dosimetry control system 6, which typically includes microprocessor 66 together with an appropriate software program, is designed to deliver Rf power at any level selected among a continuous range of Rf power levels.

The term software as used herein includes a conventional software program, a program within a programmable chip, or any other form of algorithm carried in any form of memory storage system. Referring to the block diagram of FIG. 7, Rf delivery timer 70 and photonic (light) beam delivery timer 72 are a part of the dosimetry control system, and together are adapted to deliver bi-polar RF energy between the pair of electrodes 40A–40B in a time interval that relates to a pulse train of a pulsed laser (or an intermittently delivered in relation to a CW laser delivery or non-coherent light delivery). Thus, the dosimetry control system is adapted to time "doses" of Rf current on a targeted subsurface tissue volume relative to the time of a dose of photonic (light) energy delivery.

Figure 8A:
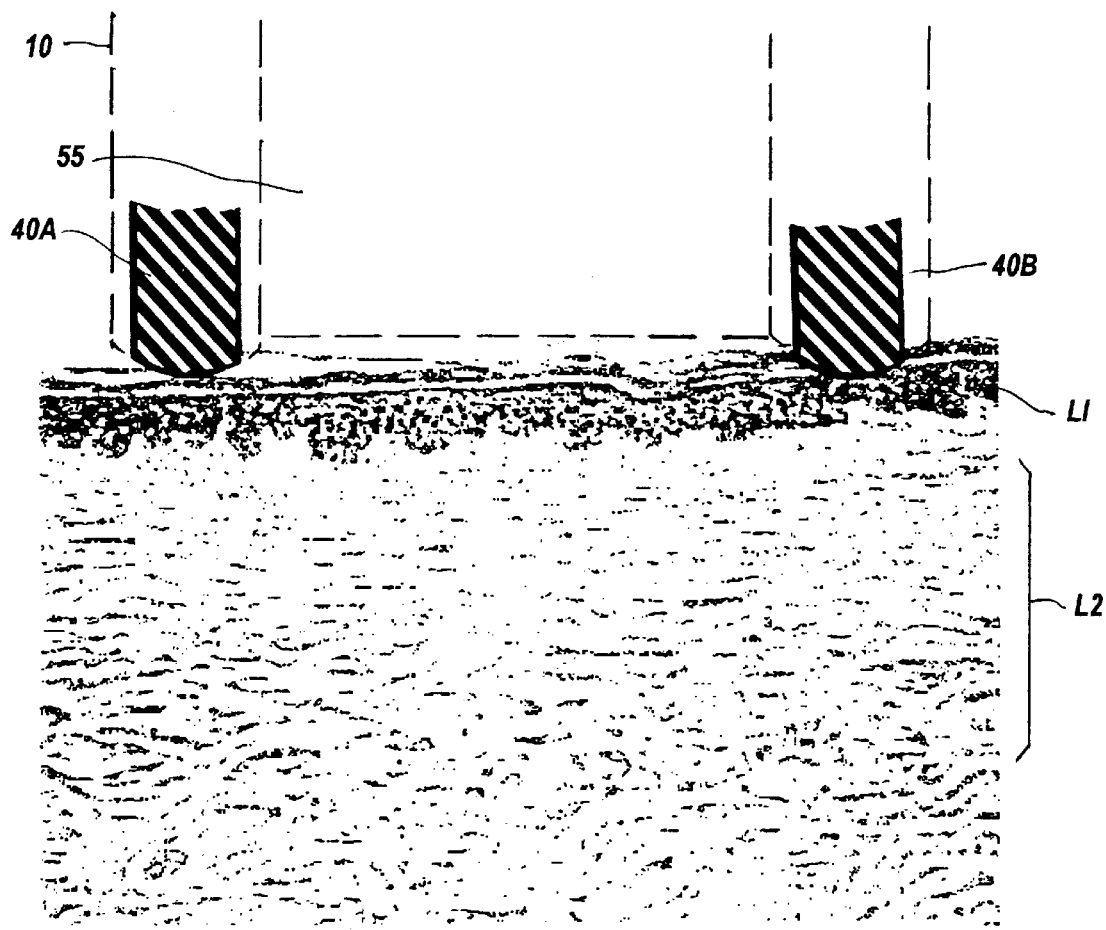
Figure 8B:
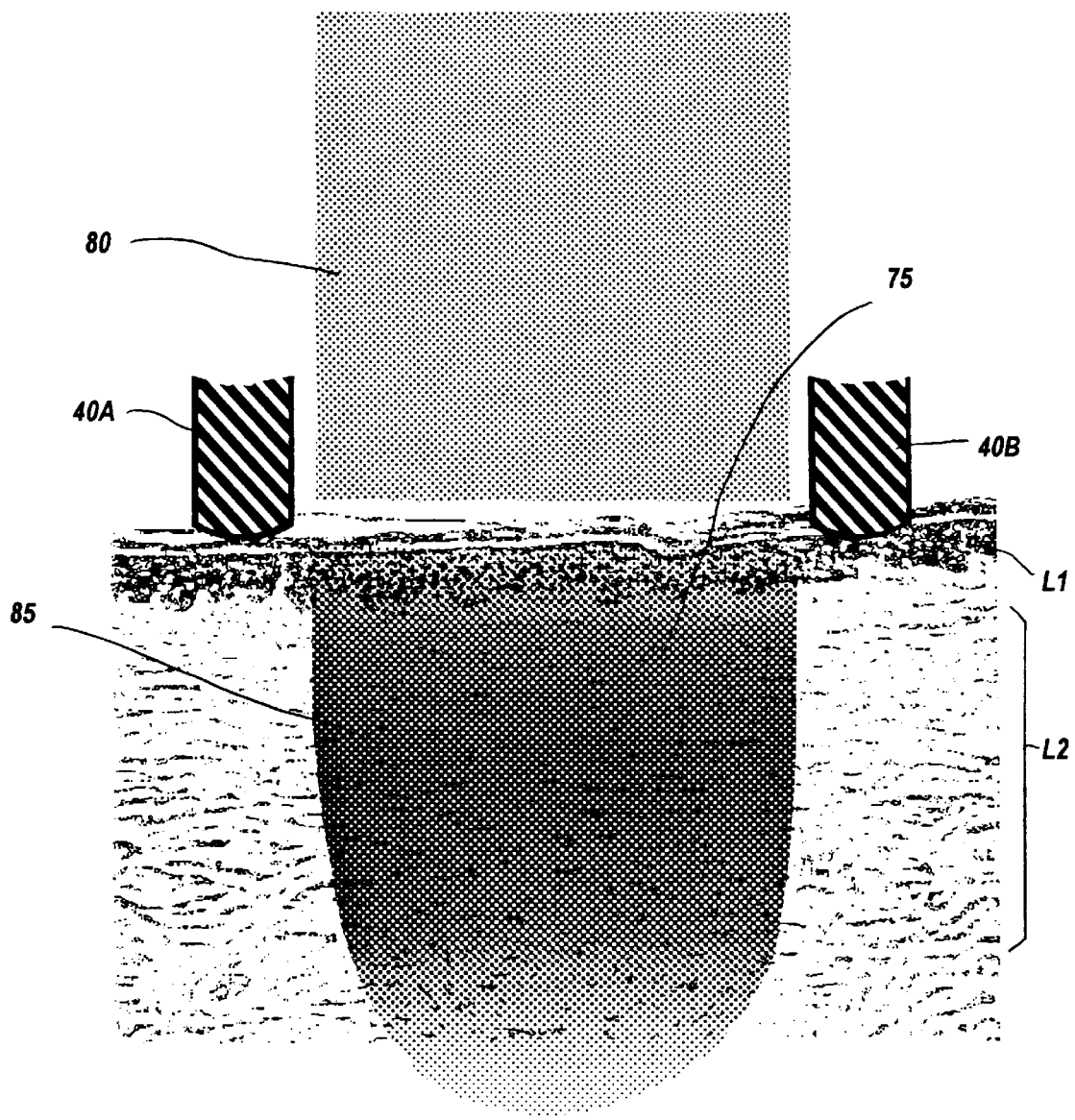
Figure 8C:
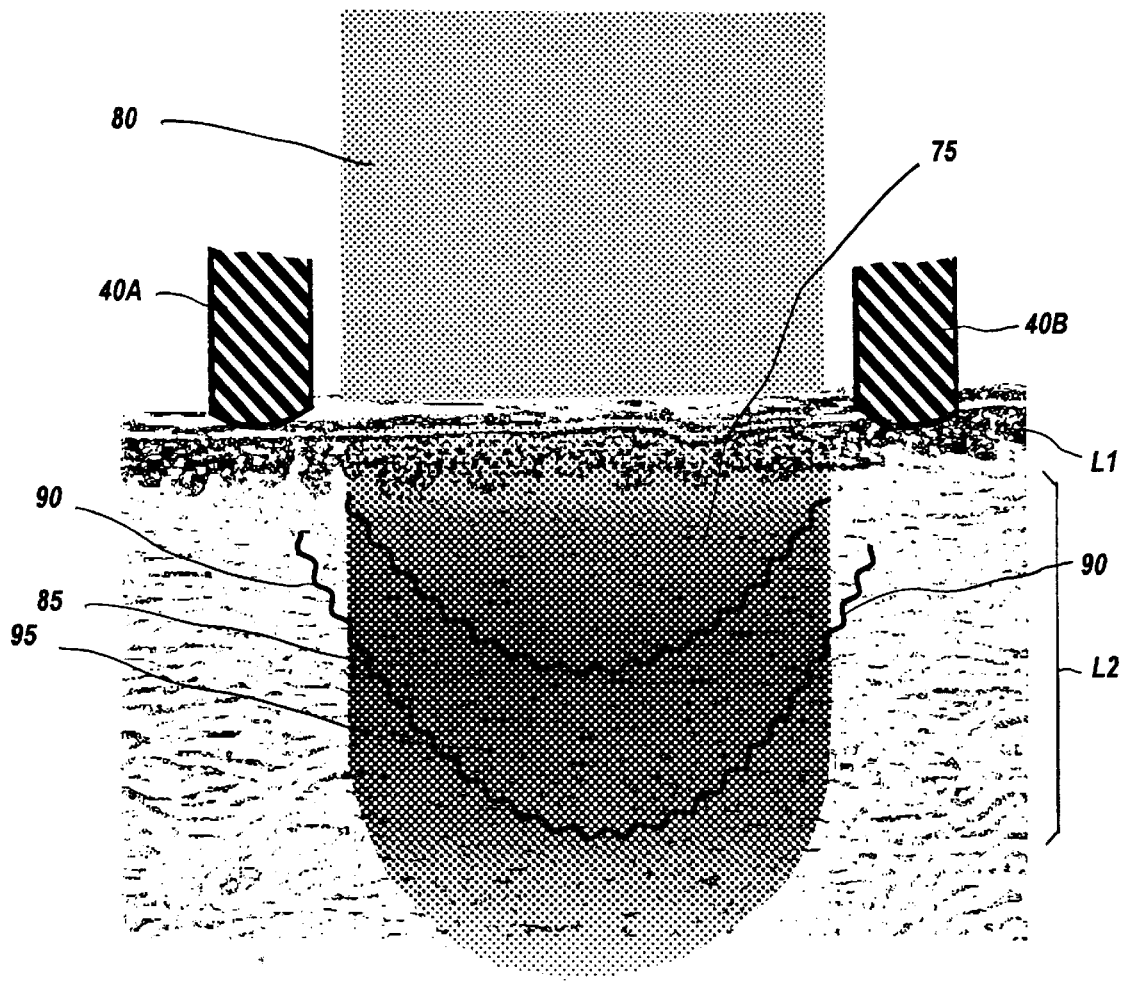
Figure 8D:
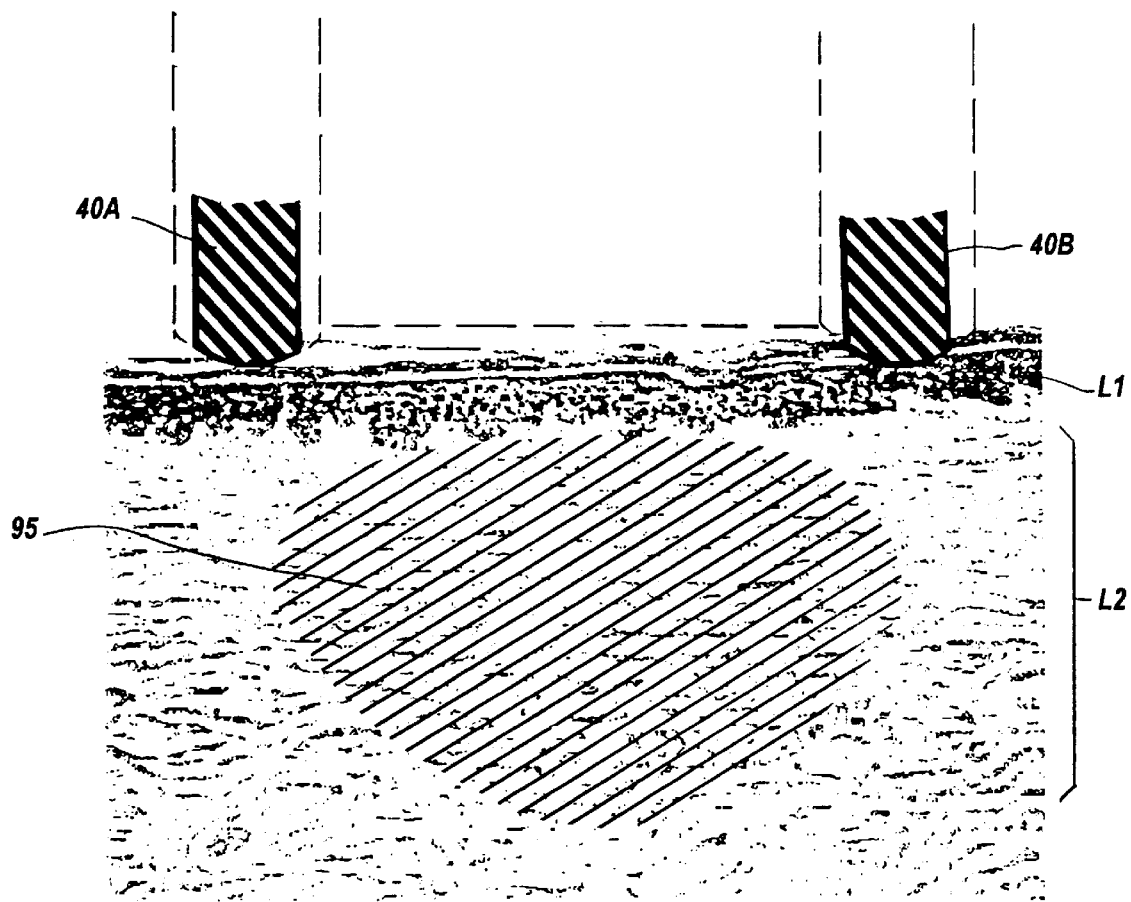

The important aspects of such an Rf dosimetry focusing system can be seen in the exemplary schematic views of FIGS. 8A–8E, wherein bi-polar Rf current flow is sequenced in on/off phases along with pulsed energy delivery of the photo (light) source. FIG. 8A shows biologic tissue with collagen matrix indicated at 75 wherein the tissue targeted for thermal treatment is shown at layer L2 for convenience underlying surface tissue layer L1. FIG. 8B depicts photon (light) source being actuated with beam 80 penetrating tissue until absorbed and extinguished in layer L2 and below wherein photon absorption and scattering creates what is termed the photoconductive effect of the invention that will cause reduction of tissue impedance to Rf flow (as well as temperature elevation) generally in the region indicated at 85 and is called a lens electrode herein. Electrode array 40 comprising paired bi-polar electrodes 40A and 40B are shown schematically in contact with surface layer L1. FIG. 8C next depicts graphically the Rf source being energized along current paths or fluence 90 (ionic perturbation) while photonic (light) source is still being energized. It can be seen that there is a "confluence" 95 indicated at intersection of beam 80 and Rf fluence 90 that enhances the effect of Rf energy delivery (i.e., focuses Rf energy delivery at the appropriate depths in layer L2). Not shown is a step wherein Rf-induced ionic perturbation continues along path or fluence 90 with the photon (light) source terminated. It should be appreciated that photon (light) source may be pulsed (at rates described above) during the continued Rf flow as depicted in FIG. 8C. FIG. 8D depicts the tissue following thermal treatment with both photon (light) beam and Rf current flow (momentarily or permanently) terminated for the particular treatment location, with hatched area depicting the tissue area where the enhanced thermal effects remain which can be contrasted with lesser thermal effects in surrounding tissue. The surface area within layer L1 generally indicates that surface cooling is accomplished by conduction of heat away from layer L1 into air, fluid or the heat sink of the material of the working end 20 of the probe (i.e., the surface zone in layer L1 exhibits lesser thermal effects).

Figure 7:
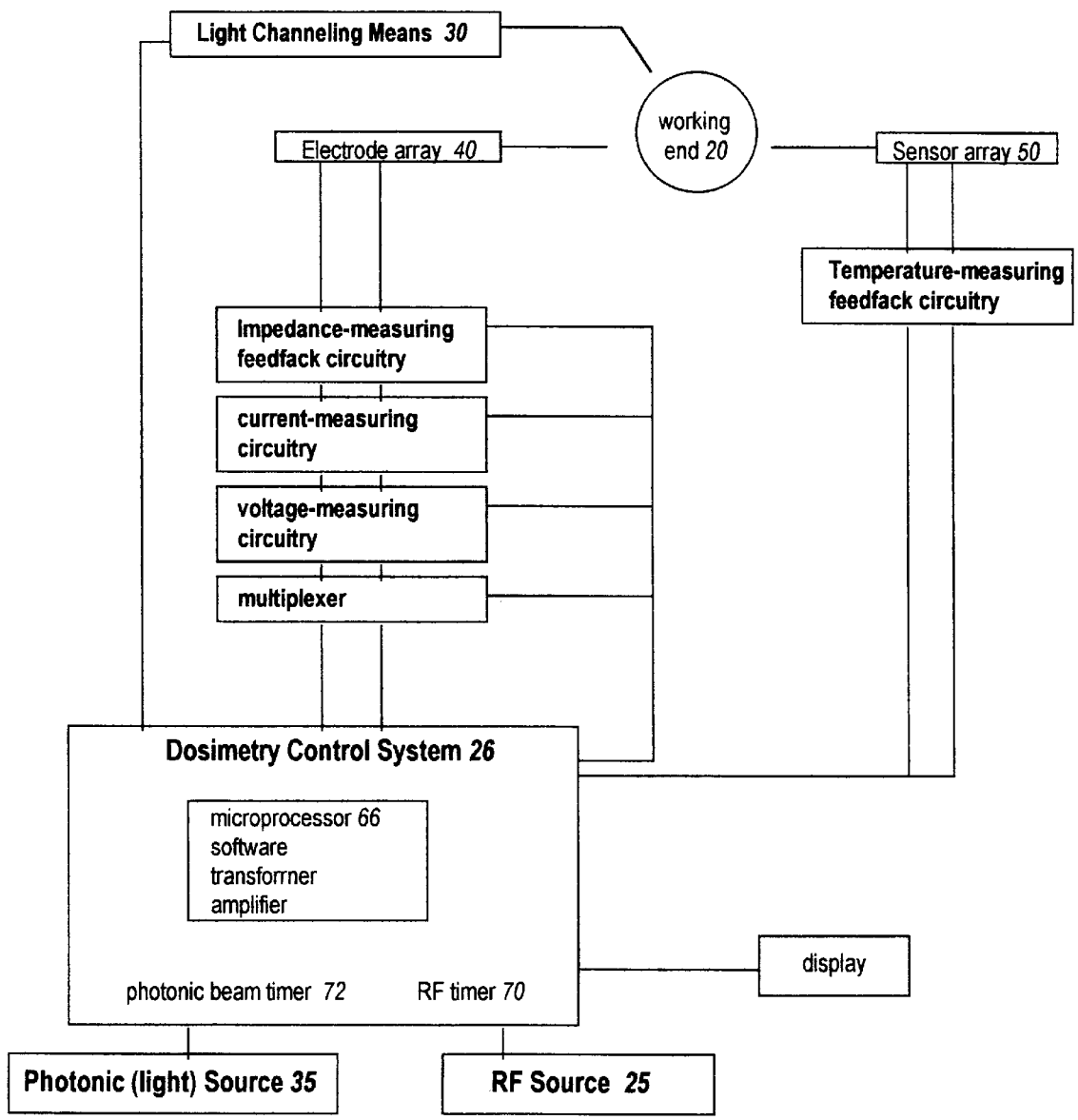
FIG. 7 is a schematic block diagram of a energy delivery sources of the present invention.

Within the hardware portion of dosimetry control system 26, there may be a keyboard, disk drive or other non-volatile memory system, displays as are well known in the art for operating the system (see FIG. 7). Transformers and amplifiers for temperature and impedance signals are typically part of the dosimetry control system. The operator interface may include various types of imaging systems for observing the treatment such as thermal or infrared sensed displays, or impedance monitoring displays.

2. Method of Use of Type "A" System

Figure 9:
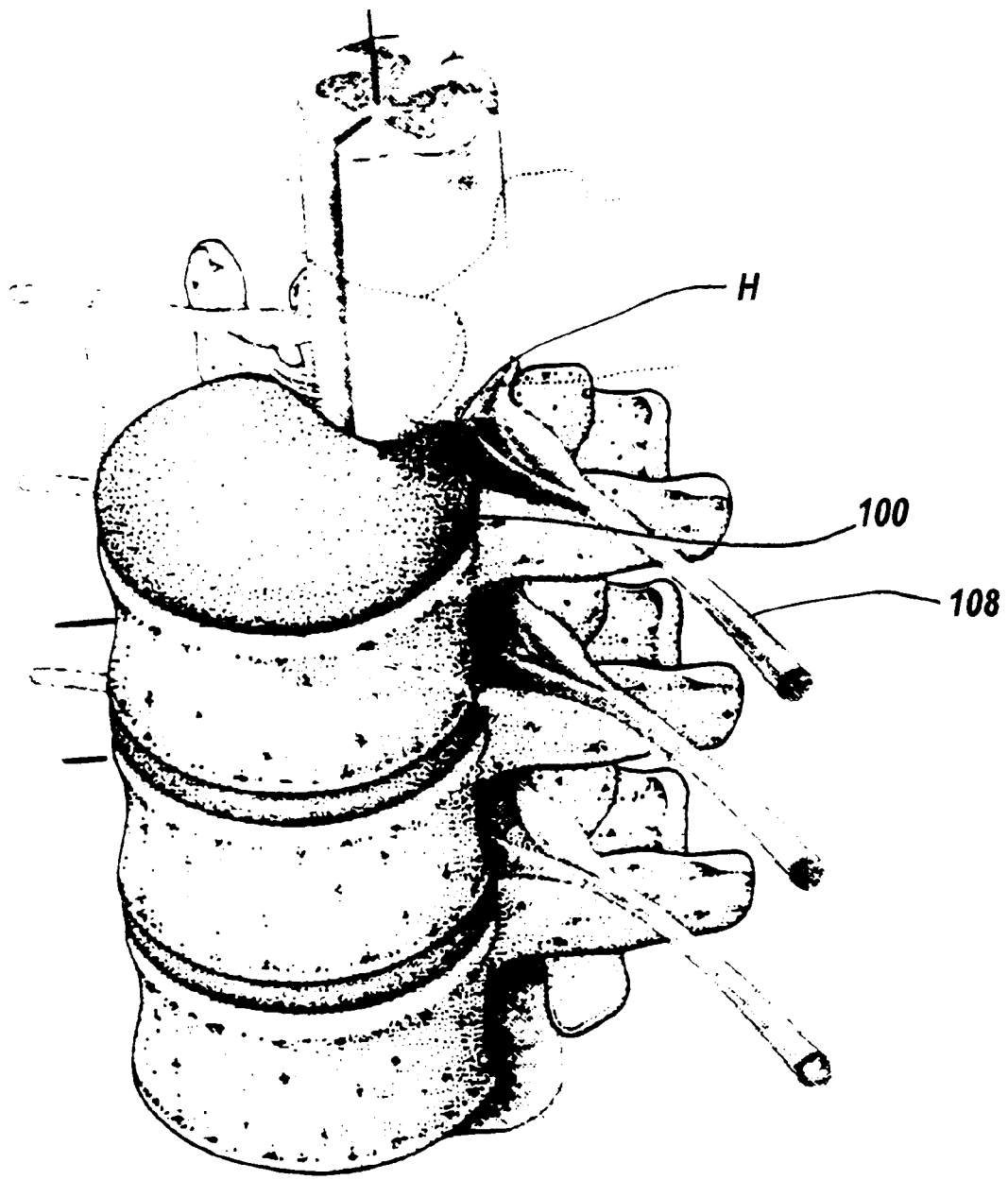
FIG. 9 is a view of a patient's spine showing a location of a herniated disc.

Operation and use of applicator 5 shown in FIGS. 9 & 10A–10C in performing a method of the present invention and can be described briefly as follows. Assume that the surgeon wishes to delivery focused thermal effects to shrink collagenous tissue in a patient's disc. FIG. 9 shows a view of a portion of the patient's spine with herniation indicated at H in disc 100.

Figure 10A:
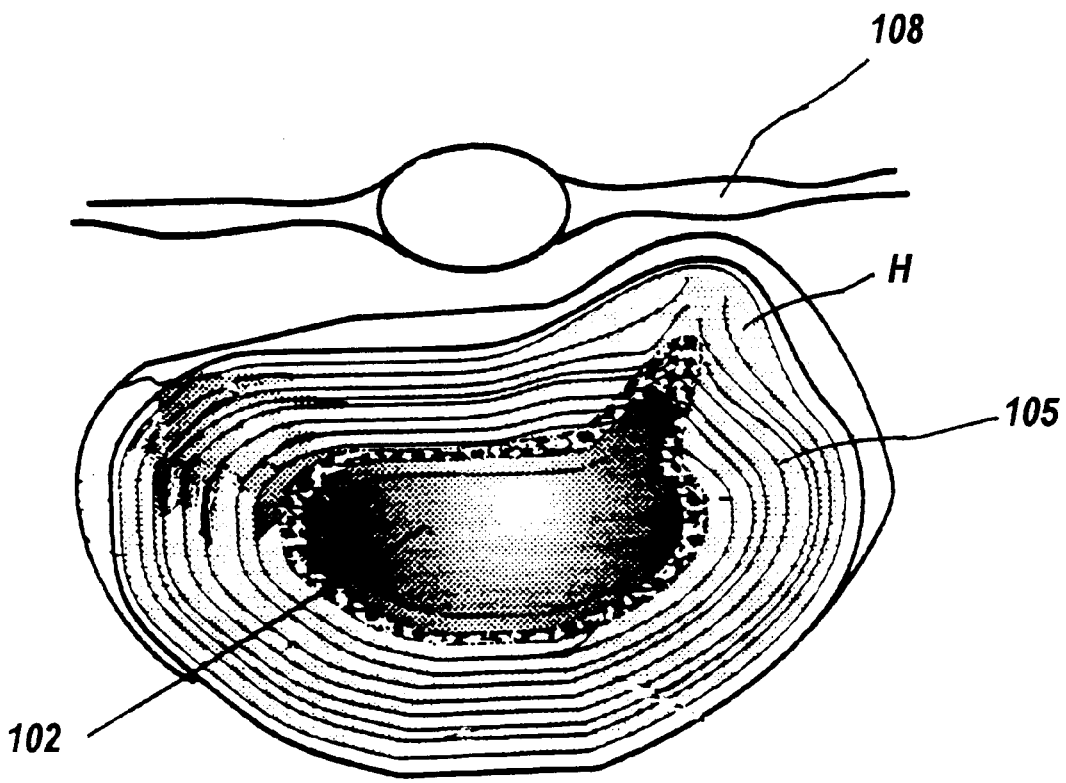
FIGS. 10A–10C are a sequence of schematic sectional representations of a herniated disc in which the device of FIG. 3 is utilized to perform a method of the invention for shrinking the collagenous annulus fibrosus.
Figure 10B:
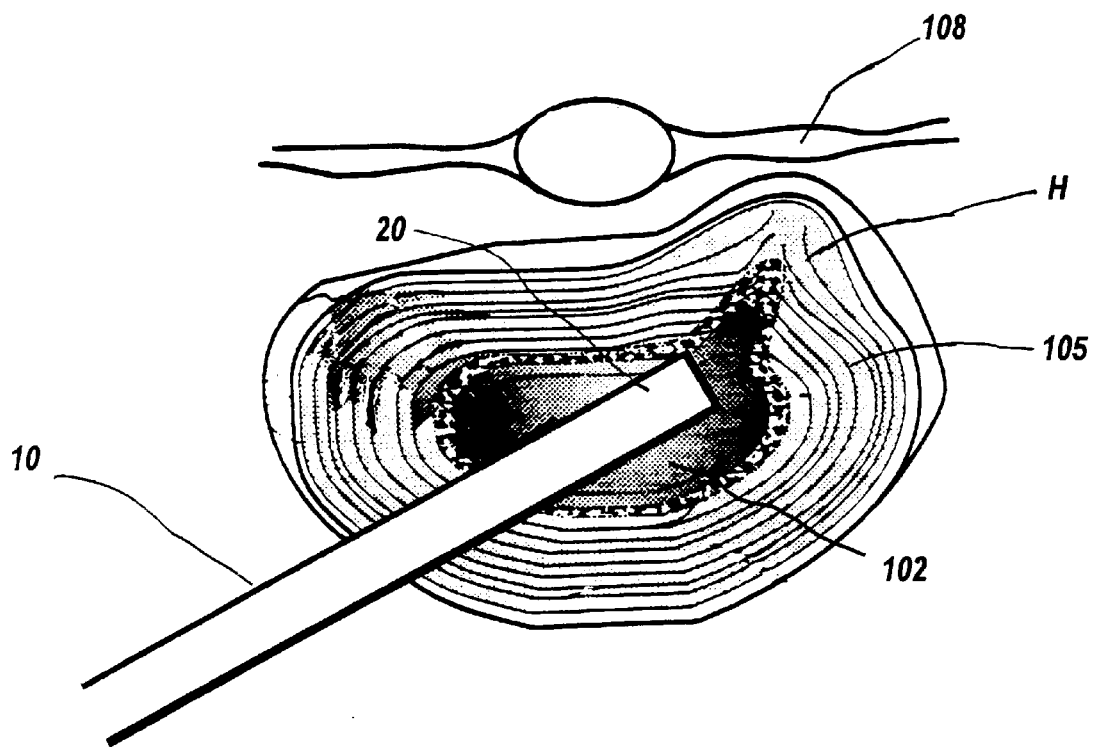
Figure 10C:
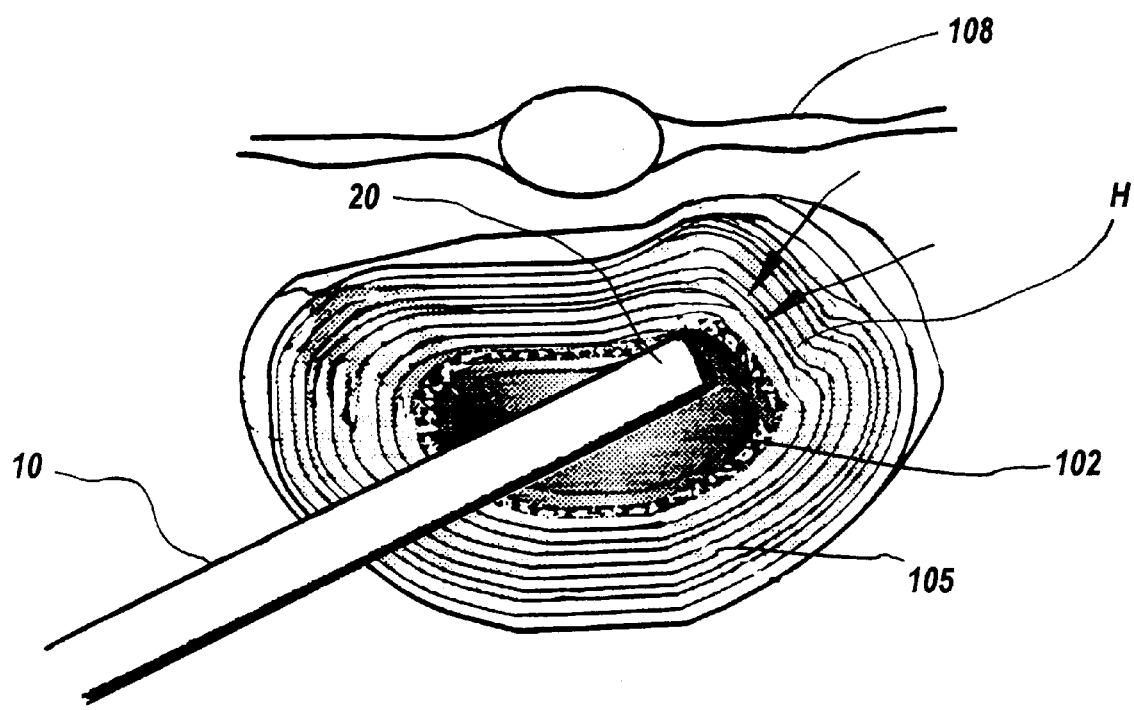

FIGS. 10A–10C show a sectional view of the nucleus propulsus 102 and annulus fibrosus 105 with herniation H causing pressure on nerve root 108. FIG. 10B shows the introduction of working end 20 through nucleus propulsus 102 to the inner surface of the annulus fibrosus to a suitable position for thermally treating the herniation indicated at H. It should be appreciated that an endoscope for viewing the treatment is not shown but is anticipated to be used (an may be incorporated into device 5 as is known in the art. With the electrodes pressed into contact with the annulus fibrosus (similar to FIG. 10B), the surgeon can actuate the phased delivery of ionothermal energy from the Rf source and photonic (light) source which treats subsurface collagenous tissue generally as shown in the schematic views of FIGS. 8B–8C. FIG. 10C shows the herniated portion of the annulus fibrosus after shrinkage which reduces pressure on nerve root 108.

By thus causing Rf current to divert to paths of least resistance along and through the tissue area comprising the "lens electrode", it is believed that Rf current intensity can be reduced significantly to achieve required levels of ionothermal effects for shrinking collagenous tissue, if compared to a mono-polar device of the prior art. The technique of the invention can thus involve holding the electrode array in a stationary position (rather than a "painting" technique) wherein the bi-polar electrodes are pressed gently against the disc surface with the Rf source delivering power ranging from 0.1 watts to 10.0 watts or more (depending on the length of time for delivery). In the preferred technique of the present invention, Rf current delivery occurs for times ranging between 1 seconds and 60 seconds to allow "low-rate" collagen shrinkage which affords the surgeon time to evaluate the extent of tissue shrinkage and to terminate Rf energy delivery based on observation. This is to be contrasted with the prior art methods of "instantaneous" collagen shrinkage which causes shrinking effects in less than 1 or 2 seconds. More preferably, the technique of the present invention will deliver Rf current ranging in power from 1 watts to 10 watts. Still more preferably, the technique will deliver Rf current ranging power from 2 watts to 5 watts. Referring again to FIG. 10B, the duration of Rf current for low-rate collagen shrinkage ranges from about 5 seconds to 40 seconds. More preferably, the technique delivers Rf current for low-rate collagen shrinkage ranging from 5 seconds to 120 seconds. With this system, the surgeon simply can terminate the low Rf power at the time the herniation shrinks to gauge the correct amount of shrinkage. After shrinking tissue in the a first location, the surgeon may move electrode array to a second location, if necessary to achieve the shrinkage desired.

Figure 11:
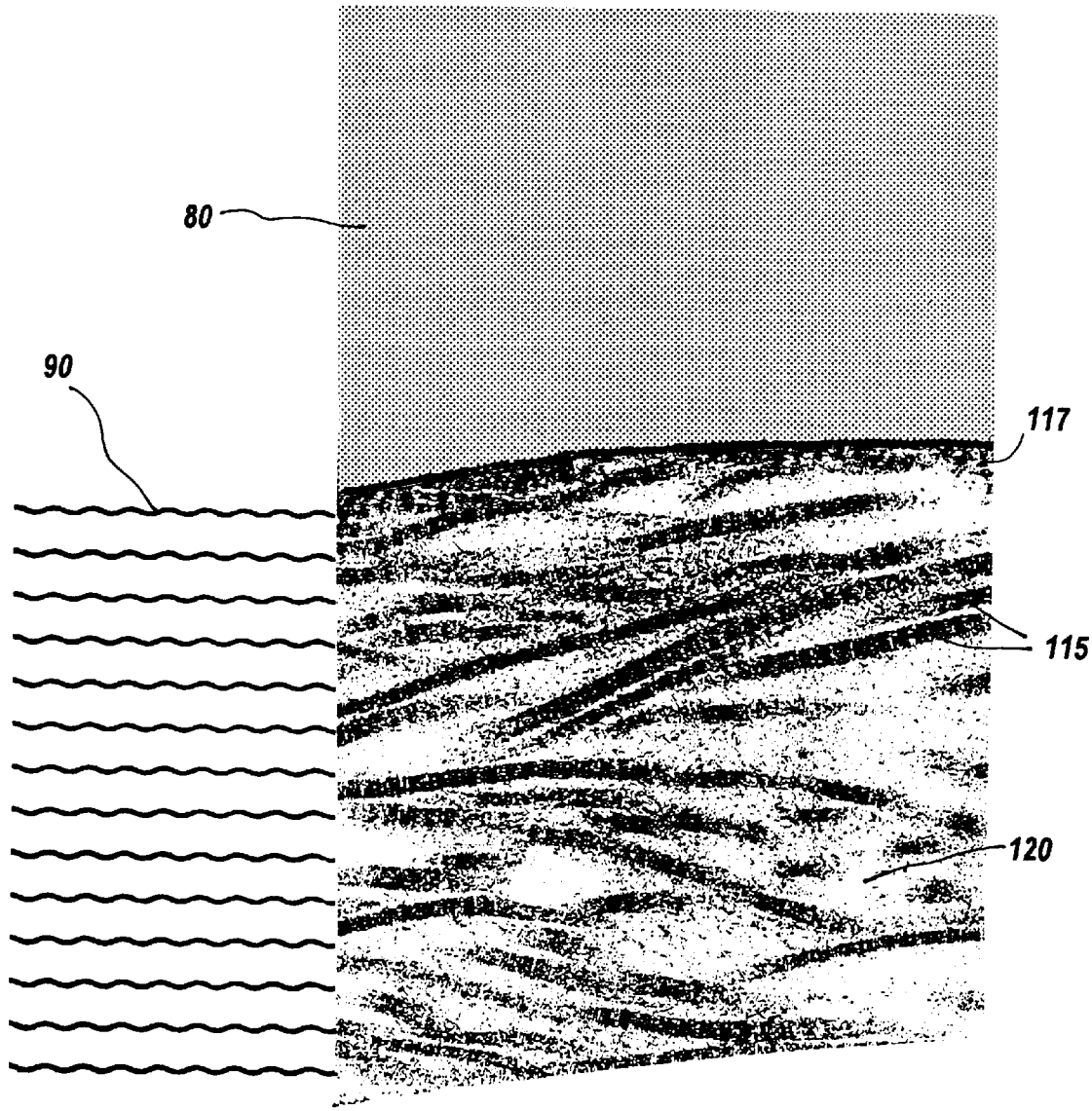
FIG. 11 is an electron micrograph showing in section a view of collagen fibrils of biologic tissue indicating what are believed to be the locations of ionothermal effects in tissue and the photoconductive effects in the tissue that are adapted to cause shrinkage of the collagen fibrils at low power levels.

Now turning to FIG. 11, a schematic indication is shown that relates to the casual mechanisms of collagen shrinkage involved in the novel method. Without wishing to be limited an particular theory to explain the effectiveness of utilizing photoconducted Rf energy to elevate the temperature of collagenous tissue with lower levels of power, it is believed that the following occurs. FIG. 11 shows an actual electron micrograph of collagen fibrils 115 underlying epithelium 117 (in a patient's cornea). Between the collagen filbrils 115 is a ground substance 120 made up of cellular structures (mostly intracellular water) and extracellular matrices. It is believed that photonic energy from light beam 80 is absorbed mostly by ground substances 120 and intracellular water which are then elevated in temperature practically instantaneously depending on the energy density created by the absorbed light. In contrast, it is believed that Rf energy indicted at fluence 90 will perturb ions mostly within the collagen fibrils and extracellular matrices (not intracellular fluids) thus elevating temperatures in a different manner that photonic energy alone. By this means, it is believed that lower levels of combined power delivery (photoconducted Rf) will elevate collagen to shrinkage temperature which will thus cause significantly less thermal spread, which is always desirable.

3. Type "B" Embodiment and Alternative Methods of Use

A Type "B" embodiment of the invention includes use of applicator 5 described of together with feedback control circuitry in dosimetry control system 26. Instead of the pre-set timed dosimetry of the first-described methods, the dosimetry control system can optionally control power delivery from both the first and second ionothermal systems in what are termed feedback-controlled operational modes. These alternative operational modes or methods of the invention can be based on feedback signals from sensor array 50 and/or electrode array 40 which generally can signal the dynamic Rf-tissue characteristics of targeted tissue during ionothermal treatment.

In a first temperature-modulating operational mode, the physician selects a target temperature level $TL_1$ at the surface tissue layer which typically is a particular temperature below the temperature that will desiccate or ablate such surface tissue. Temperature signals measured by thermal sensor array 50 are continuously fed to dosimetry control system 26 through temperature feedback circuitry to control the level of Rf delivery to the paired opposing electrodes. The dosimetry control system thus can measure the difference between the actual temperature measured (or averaged) by sensor array 50 and the target temperature level $T_1$, and thereafter select a power delivery level or delivery profile (power over time) proportionate to the temperature difference at any point in time during a treatment cycle. The control system 26 further can be programmed to control power delivery based on temperature signals such that if a particular temperature is exceeded at any sensor location the power delivery will be terminated. The physician further can set a target temperature level $TL_1$ which can be maintained at a particular sensor site or averaged among several sensor sites. The control system 26 further has a timing device (not shown) to provide the physician with the capability of maintaining a particular temperature at any electrode site (or combination thereof in cases of more than two electrodes) for a particular length of time. As mentioned above, a power delivery profile can be programmed into dosimetry control system 26 to deliver energy over a period of time to achieve a target temperature level or the dosimetry control system can accept a time pre-set for reaching a particular temperature level.

As mentioned above, the dosimetry control system circuitry and sensor array circuitry has a temperature pre-set capability that can terminate or modulate Rf delivery (and multiplex or vector current in the case of more than two electrodes), when a temperature at particular sensor location site is exceeded. In accordance with this aspect of the invention, the temperature-modulating operational mode may includes a Rf delivery vectoring mode in cases where the working end is configured with multiple electrodes. In other words, the dosimetry control system 26 further includes circuitry for Rf current delivery that is responsive to temperature levels and signals from particular sensor sites wherein the controller can multiplex or sequence Rf current to paired electrodes (or combinations thereof) where sensed temperatures are below pre-set levels thus further helping to prevent surface desiccation around particular electrode and sensor locations.

In a second manner of operation or impedance-controlled operational mode, dosimetry control system 26 can be programmed to receive signals and values for tissue impedance which typically include a maximum impedance or resistance level estimated or known for the target tissue and a minimum impedance or resistance level (also known or estimated). This feedback circuitry or impedance-measuring circuitry is adapted to measure impedance levels for controlling power delivery through the control system. The impedance-measuring circuitry converts current and voltage signals (see FIG. 7) into an actual impedance level and signal and is responsive to the Rf current flowing through any paths in target tissue between electrode combinations and to the Rf voltage connected across the path through tissue between the particular electrodes. As shown in FIG. 7, a current measuring device (e.g., a transformer) and a voltage measuring device are operatively connected to dosimetry control system 26 on the energy delivery side and electrode array 40. The dosimetry control system 26 is responsive to a signals generated by the impedance-measuring circuitry for controlling Rf energy delivered to the electrode array via multiplexer 96. The impedance-measuring circuitry also is coupled to the electrode array 40 via the multiplexer for measuring the impedance of targeted tissue along any particular path between operating electrodes and feed continuous signals to dosimetry control system 30. Typically, the controller 30 selects a particular impedance or resistance level between the maximum and minimum impedance levels and turns off or modulates Rf power delivery to any particular paired electrodes when the impedance reaches the particular level as it rises toward the maximum impedance level. For example, the particular impedance level may be an average level between the selected maximum and minimum impedance levels. In this impedance-controlled operational mode, the sequencing circuitry for vectoring current previously described can be responsive to the impedance levels between particular electrodes as well as temperature levels at the sensor sites and the controller can be adapted to multiplex or sequentially vector energy delivery between particular paired electrodes only where impedance levels are within predetermined parameters to further insure against blistering or desiccation of the epithelium.

In a third manner of controlled energy delivery, the controller may also operate in a combination temperature/impedance-controlled operational mode to still more precisely control Rf power delivery which combines the above described features. All of the above-described control modes can be combined to select a preferred particular temperature (or average) at one or more sensor locations in the working end 20 such that Rf energy delivery will be terminated if a maximum pre-set temperature is reached. The impedance controlled mode may be incorporated as previously described to modulate or control power delivery based on impedance levels to achieve a particular sensed temperature or temperature profile. Thus, the temperature at the sensor array can be maintained at a the pre-set temperature based on impedance feedback unless a maximum temperature is exceeded, at which energy delivery again is modulated or terminated.

The dosimetry control system 26 and software together with the above described feedback circuitry thus are capable of full process monitoring and continuous control of following operational variables: (i) power delivery; (ii) time, temperature and impedance parameters of a selected treatment cycle; and (iii) multiplexing or vectoring Rf current delivery between and among individual electrodes. A microprocessor can constantly monitor all operational variables and the dosimetry controller software may typically operate in a temperature-controlled method where all functions are varied depending on temperature signals from sensor array 40. The above-listed operational variables can be controlled and varied in response to tissue temperatures measured at multiple sites on tissue surfaces as well as by impedance to current flow as measured between any particular paired electrodes which indicates the current carrying capability of the tissue during the treatment process. Additionally, dosimetry control system 26 besides multiplexing Rf current between particular electrodes can monitor circuit continuity for each electrode and even determine which electrode is delivering energy at any moment in time. The microprocessor can sequentially receive and store digital data representing impedance and temperature values and the temperature and impedance values also may be displayed on operator interface as numerical values. The temperature and impedance values are compared by the microprocessor with pre-programmed temperature and impedance limits as described above and when the measured temperature value or impedance value at a particular site exceeds a pre-determined limit, a warning or other indication can be given on the operator interface (such a warning light) while at the same time the delivery of energy to a particular electrode site can be decreased or multiplexed to another electrode or electrode pair. Calculated surface temperatures of tissue in recessed portion 30 may be forwarded by the dosimetry control system to a display and compared to a predetermined limit to activate a warning indicator on the display.

4. Ionothermal Systems for Treating Other Biological Tissues

Figure 12A:
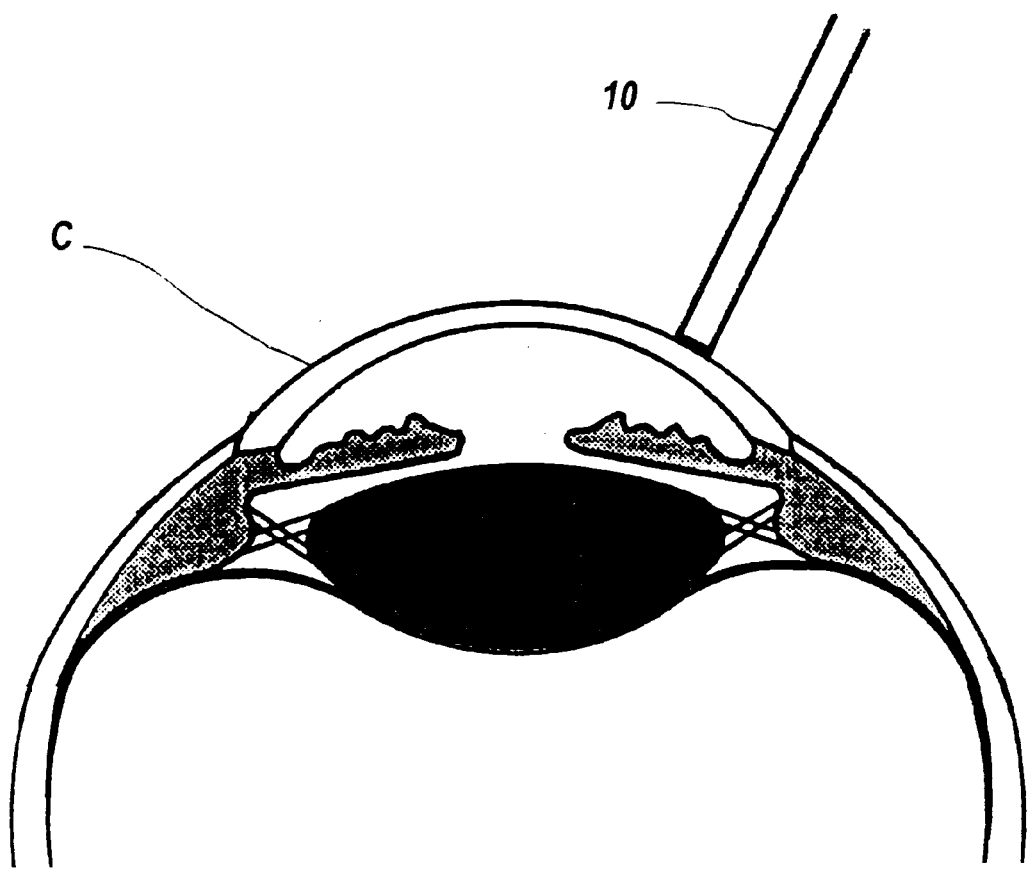
FIGS. 12A–12C are views showing the manner in which the device similar to that of FIG. 3 may be utilized to perform a method of the invention in photoconducted Rf delivery to coagulate tissue or shrink collagenous layers in a patients' cornea for refractive purposes.
Figure 12B:
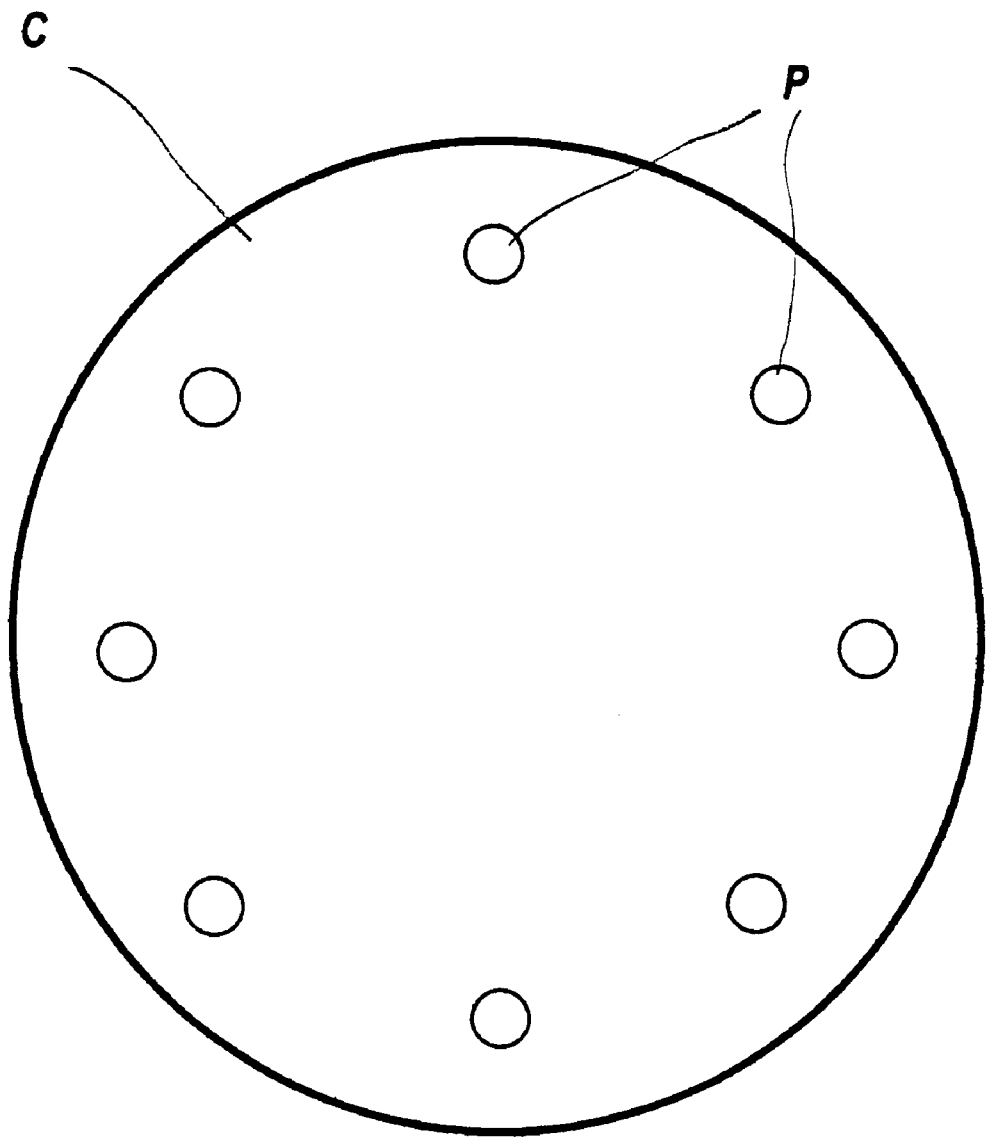
Figure 12C:
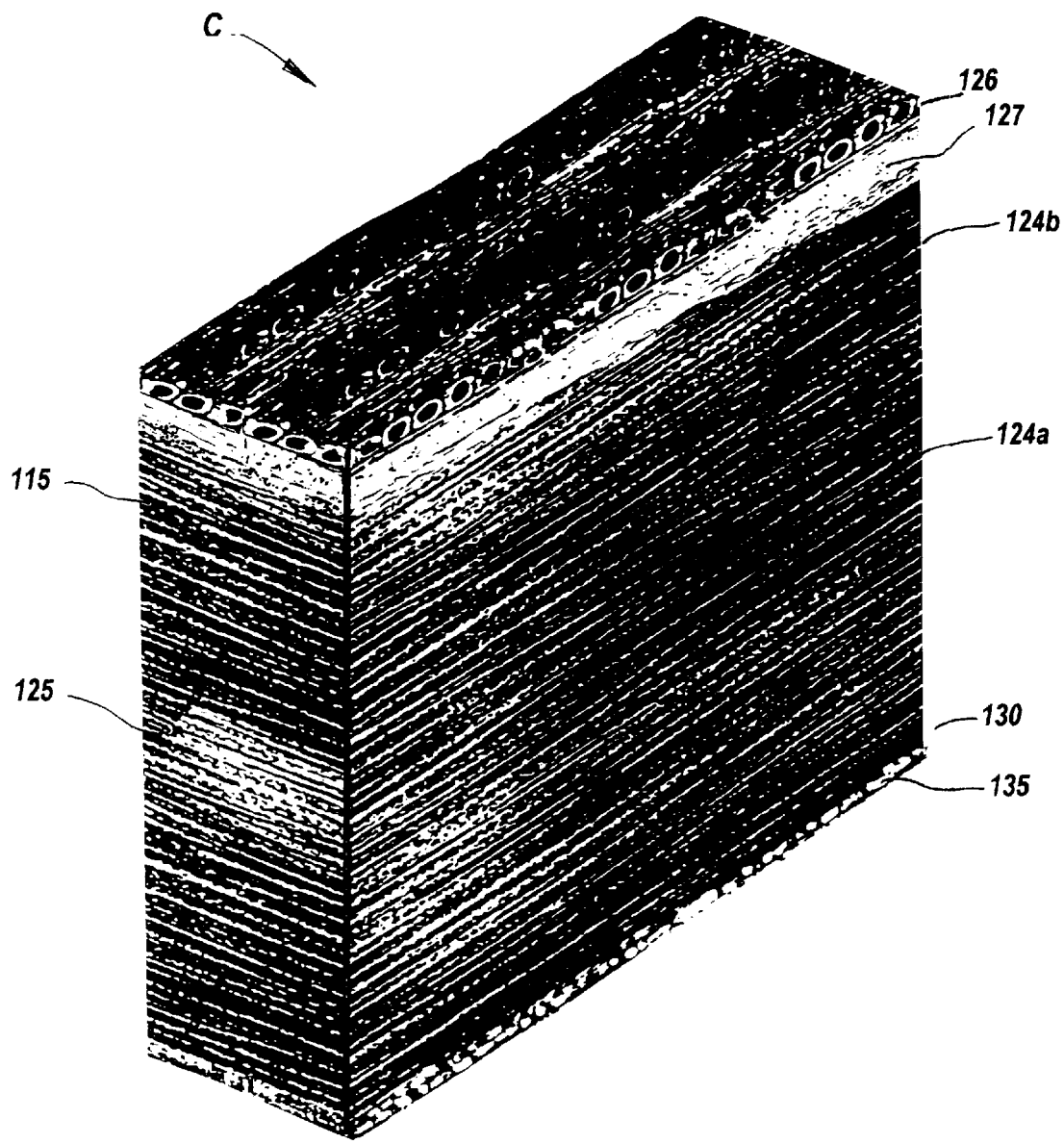

It should be appreciated that the combined use of Rf energy delivery system together with light (e.g., laser) energy for creating a photoconductive effect for focusing Rf delivery was conceived of for ionothermal keratoplasty for refractive corrections of the eye. More specifically, the collagen-containing stroma of the cornea C outside the eye's visual axis can be thermally treated to elevate the temperature of collagen fibrils to melt such fibrils, to shrink such fibrils or to damage keratocytes therein, depending on the temperature level attained, for example from 45° to 70° C. In the use such a system for changing the shape of a cornea C, (herein referred to as ionothermal keratoplasty (optically stimulated)), the probe 5 is used to contact the surface of the cornea in a number of positions P radially around the cornea, for example about 8 to 12 radial locations as indicted in FIGS. 12A–12B. The objective of the treatment, referring to FIG. 12C, is to deliver focused Rf energy delivery (focused by photoconductance effect) to the mid-stroma 124_a_ or midanterior stroma 124_b_ to coagulate tissue (a hybrid Rf-photocoagulation modality), or to melt or shrink collagenous tissue in stroma 125 (collagen fibrils indicated at 115). FIG. 12C shows a section of a patient's cornea with epithelium 126 overlying Bowman's membrane 127 and stroma 125. Descemet's membrane and the endothelial layers are indicated at 130 and 135 respectively. In such an embodiment, the light beam wavelength for developing an optimal photoconductive effect in patient's cornea is preferably in the range of 1.30 microns to 1.70 microns to provide an extinction depth in cornea from about 0.01 mm. (100 microns) to 0.04 mm. (400 microns) which would be in the mid-anterior to mid-stroma. The spot size may be from about 0.25 mm. to 1.0 mm. with other parameters as described above. Another manner of stating the preferred wavelength parameters would be to state that the light energy source would produce a light beam having a wavelength such that the light beam's absorption coefficient when passing through water ranges from about 9.0 cm.$^{-1}$ to 12.0 cm.$^{-1}$.

It should be appreciated that the system of the invention may be utilized in various other configurations, for example in the form of a probe with the distal end having any suitable dimension from 1 mm. to 5 mm. or more in diameter with a plurality of electrodes and light channel in at the center of the working end. The applications of such a system may be ionothermal treatment of collagenous tissues, for example, in cartilage, joint capsules, airway tissues, dermal or subdermal tissues, tympanic membranes, strabismus muscles or other collagen-containing tissues.

Applications of the Rf energy source in combination with the photonic energy source of the present invention may be generalized to deliver controlled levels of Rf energy along with a photoconductance effect to subsurface tissues at other locations in a body for shrinking collagenous tissues or for other therapeutic purposes (eg., bio-stimulation or bio-excitation). Although particular embodiments of the present invention have been described above in detail, it will be understood that this description is merely for purposes of illustration. Specific features of the invention are shown in some drawings and not in others, and this is for convenience only and any feature may be combined with another in accordance with the invention. Further variations will be apparent to one skilled in the art in light of this disclosure and are intended to fall within the scope of the appended claims.

What is claimed is:

1. A system for ionothermal treatment of biological tissue which is the object of treatment, comprising:

paired bi-polar electrodes at a distal end of a probe member, each said electrode having an exposed surface for positioning in contact with said biological tissue;

an Rf source for generating radiofrequency energy operatively connected to said paired bi-polar electrodes;

a light-channeling structure within said probe member for directing a light beam toward said biological tissue; and a light energy source for producing a light beam which has a wavelength such that the light beam's absorption coefficient when passing through water ranges from 0.01 cm.$^{-1}$ to 115.0 cm.$^{-1}$, said light source operatively connected to said light-channeling structure.

2. The system of claim 1 wherein said light energy source produces a light beam having a wavelength such that the light beam's absorption coefficient when passing through water ranges from 10.0 cm.$^{-1}$ to 12.0 cm.$^{-1}$.

3. A system for ionothermal treatment of biological tissue which is the object of treatment, comprising:

at least one pair of bi-polar electrodes at a distal end of a probe member, each said electrode having an exposed surface for positioning in contact with said biological tissue;

an Rf source for generating radiofrequency energy operatively connected to said at least one pair of bi-polar electrodes;

a light-channeling structure within said probe member for directing a light beam toward said biological tissue; and a photonic energy source for producing a light beam which has a wavelength ranging from 1.3 microns to 1.7 microns, said photonic energy source operatively connected to said light-channeling structure.

4. The system of claim 3 wherein said photonic energy source produces a light beam having a wavelength ranging from 1.4 microns to 1.55 microns.

5. A method for ionothermal treatment of biological tissue which is the object of treatment utilizing a device having a working interface carrying at least one pair of bi-polar electrodes together with a light-channeling structure within said working interface for directing a light beam toward said biological tissue, comprising the steps of:

positioning said working interface and at least one pair of bi-polar electrodes in contact with a tissue surface overlying a targeted biological tissue volume;

actuating a photonic energy source to delivery a light beam having a wavelength ranging from 1.3 microns to 3.0 microns through said light-channeling structure to thereby irradiate said targeted biological tissue and creating a photon-induced energy density therein; and actuating an Rf source to deliver Rf energy to said at least one pair of bi-polar electrodes thereby providing an Rf-induced energy density in the biologic tissue already having a photon-induced energy density created therein.

6. The method system of claim 5 wherein the biologic tissue is a collagenous tissue.

7. The method system of claim 6 wherein the biologic tissue is an annulus propulsus.

8. The method system of claim 7 wherein the biologic tissue is a the stroma of a cornea.

9. The method system of claim 7 wherein the biologic tissue is a cartilage of a joint capsule.

* * * * *